(12) United States Patent
Hariri et al.

(10) Patent No.: US 10,166,082 B1
(45) Date of Patent: Jan. 1, 2019

(54) SYSTEM AND METHOD FOR CONTROLLING A ROBOTIC WRIST

(71) Applicant: Verb Surgical Inc., Mountain View, CA (US)

(72) Inventors: Alireza Hariri, Berkeley, CA (US); Sina Nia Kosari, Fremont, CA (US)

(73) Assignee: VERB SURGICAL INC., Mountain View, CA (US)

( * ) Notice: Subject to any disclaimer, the term of this patent is extended or adjusted under 35 U.S.C. 154(b) by 0 days.

(21) Appl. No.: 15/983,946

(22) Filed: May 18, 2018

(51) Int. Cl.
- *A61B 34/37* (2016.01)
- *A61B 34/00* (2016.01)
- *A61B 34/35* (2016.01)
- *B25J 9/16* (2006.01)
- *A61B 34/30* (2016.01)

(52) U.S. Cl.
CPC .............. *A61B 34/71* (2016.02); *A61B 34/25* (2016.02); *A61B 34/35* (2016.02); *B25J 9/1633* (2013.01); *A61B 34/77* (2016.02); *A61B 2034/305* (2016.02); *G05B 2219/39322* (2013.01)

(58) Field of Classification Search
CPC ......... A61B 34/35; A61B 34/37; A61B 34/70; A61B 34/71; A61B 34/77; B61B 2034/305; B61B 2034/715; B25J 9/1633; B25J 9/1646; B25J 9/1694; G05B 2219/39321; G05B 2219/39322; G05B 2219/39327; G05B 2219/39329; G05B 2219/39331; G05B 2219/39333
See application file for complete search history.

(56) References Cited

U.S. PATENT DOCUMENTS

| | | | |
|---|---|---|---|
| 2003/0036748 A1* | 2/2003 | Cooper | A61B 17/00234 606/1 |
| 2008/0046122 A1 | 2/2008 | Manzo et al. | |
| 2008/0154246 A1* | 6/2008 | Nowlin | G16H 50/50 606/1 |
| 2009/0088775 A1 | 4/2009 | Swamp et al. | |
| 2010/0087835 A1* | 4/2010 | Blumenkranz | A61B 90/10 606/130 |
| 2015/0150635 A1 | 6/2015 | Kilroy et al. | |
| 2016/0303743 A1 | 10/2016 | Rockrohr | |

OTHER PUBLICATIONS

International Search Report dated Aug. 24, 2018 for International Application No. PCT/US2018/033478.
Written Opinion dated Aug. 24, 2018 for International Application No. PCT/US2018/033478.

* cited by examiner

*Primary Examiner* — Spencer D Patton
(74) *Attorney, Agent, or Firm* — Brinks, Gilson & Lione

(57) ABSTRACT

A system for controlling a surgical robotic tool having an end effector driven by actuators through antagonistic cables is disclosed. The control system may include a position controller and a grip force controller. The position controller may be configured to receive an input signal to control the position of the end effector and generate a first command to drive the actuators to move the end effector. The grip force controller may be configured to receive another input to control the force exerted by jaws of the end effector and generate a second command. The first command and the second command may be combined to generate a composite command that is provided to the actuators to drive motion of the end effector. A third current or position command may be generated by a slack controller to prevent cable slack.

14 Claims, 10 Drawing Sheets

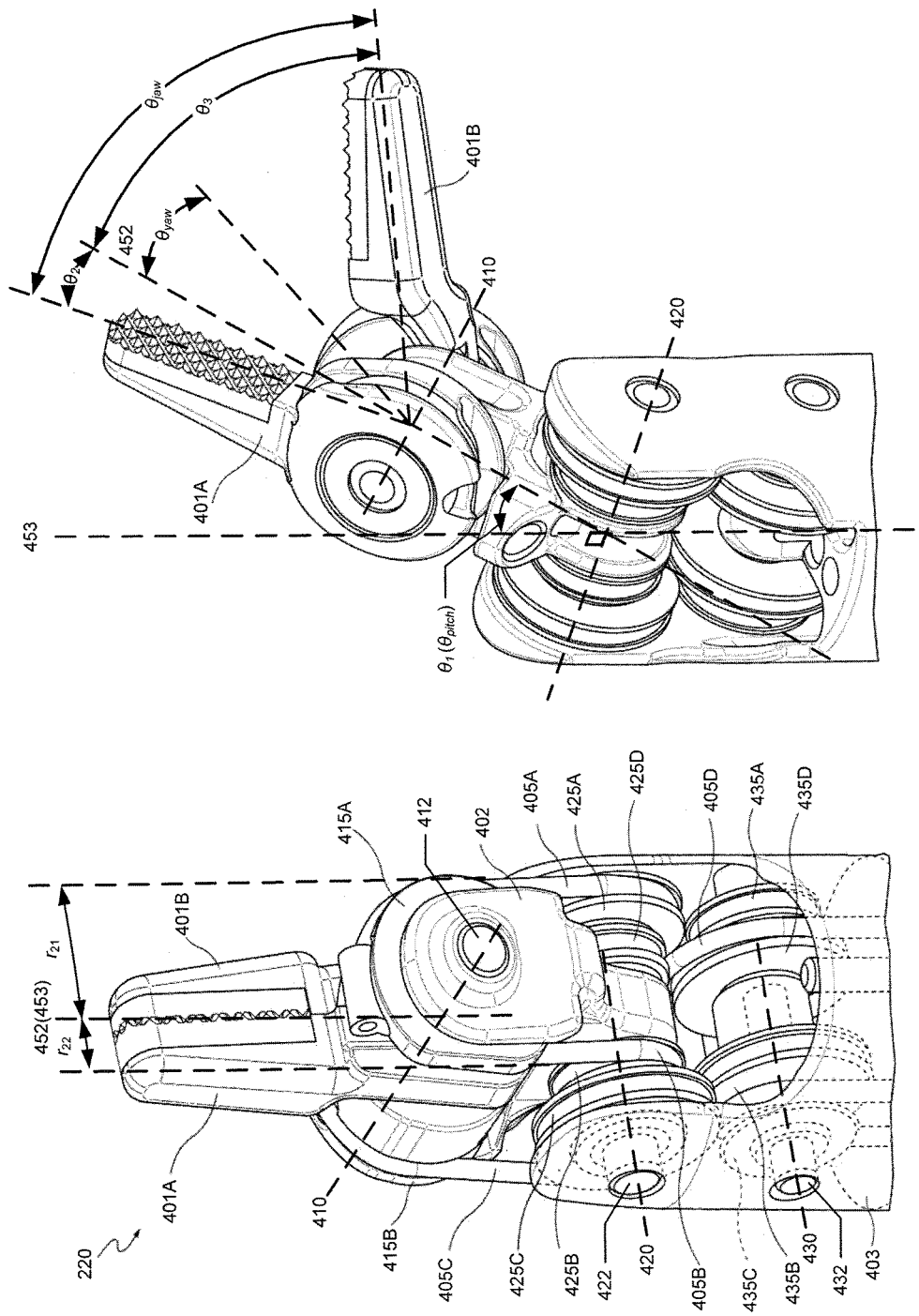

1000

```
┌─────────────────────────────────────────────────────────────────────┐
│ Receive Input To Effect A Desired State Of End Effectors Of Surgical │
│ Robotic Tool, Input Including At Least One Of Pitch Angle Of Robotic │
│ Wrist, Yaw Angle Of End Effector And Jaw Angle Between Two Jaws Of   │
│ End Effector Each Manipulated By At Least One Actuator               │
│                            1002                                      │
└─────────────────────────────────────────────────────────────────────┘
                                  │
                                  ▼
┌─────────────────────────────────────────────────────────────────────┐
│ Determine Desired Position Of End Effector Based On Pitch Angle And  │
│ Yaw Angle Commands, And Desired Grip Force Between Two Jaws          │
│                    Based On Jaw Angle                                │
│                            1004                                      │
└─────────────────────────────────────────────────────────────────────┘
                                  │
                                  ▼
┌─────────────────────────────────────────────────────────────────────┐
│ Drive The At Least One Actuator To Effect Desired Position Of End    │
│      Effector And Desired Grip Force Between Two Jaws                │
│                            1006                                      │
└─────────────────────────────────────────────────────────────────────┘
```

SYSTEM AND METHOD FOR CONTROLLING A ROBOTIC WRIST

TECHNICAL FIELD

This invention generally relates to robotics and control systems, and more specifically to systems and methods for controlling positions and grip force of end effectors of robotic surgical tools.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulae for providing access to the patient's body cavity and organs, etc. In robotic MIS systems, it may be desirable to establish and maintain high positional accuracy for surgical instruments supported by the robotic arms.

New class of surgical instruments supported for robotic arms may share similar designs, for example, a tool may have an end effector that comprises a robotic wrist and one or more jaws, and a pulley and cable system for coupling the end effector to actuators in a tool drive, which can drive multi-axial motions (e.g., pitch and yaw) of the end effector. The end effectors may include more than one jaws actuated through antagonistic cables to perform grasping, cutting, suturing, among other surgical tasks. The ability to control the grip force between the jaws, while moving the robotic wrist to any angular position with precision, is a fundamental requirement for the usability of the robotic surgical instruments. There is currently no known method that can achieve this with a four-wire antagonistic robotic wrist.

SUMMARY

Generally, in some variations, a system and method for controlling during robotic surgery a robotic surgical tool having an end effector at a distal end. The end effector may have a robotic wrist and two members coupled to the robotic wrist pivoting relative to each other, each member is robotically manipulated via a pair of antagonistic cables imparting forces when tensioned. The system receives an input for a desired state of the end effector and calculates a displacement of the pair of the antagonistic cables for each member of the end effector based on the desired state. The system next generates a first command for driving the robotic wrist and the end effector members based the calculated displacement. The system then determines whether the desired state includes a desired grip force between the two end effector members. In response to a determination of the desired grip force, the system generates a second command for tensioning at least one of the pair of antagonistic cables for a member of the end effector based on the desired grip force and the current grip force between the two end effector members. The system further drives the end effector to effect the desired state based on the first command and/or the second command.

In some variations, the desired state comprises at least one of a desired pitch angle of the robotic wrist, a desired yaw angle of the end effector and a desired jaw angle between the two opposing members of the end effector, wherein determining whether the desired state include a desired grip force comprises comparing the desired jaw angle to a threshold. The threshold is a contact jaw angle between the two opposing members of the end effector when grasping an object or when in contact to each other without grasping any objects, wherein the contact jaw angle is determined based on an estimation of the current grip force between the two opposing members and an estimation of current jaw angle. The current grip force between the two end effector members is estimated based on the measurements of current tensioning forces on the pair of antagonistic cables.

In some variations, each of the pair of antagonistic cables is tensioned by at least on actuator and calculating the displacement comprises measuring current positions and/or velocity of the at least one actuator and current tensioning forces on the pair of antagonistic cables; and estimating a current state of at least one of a pitch angle of the robotic wrist, a yaw angle of the end effector, and a jaw angle between the two opposing members of the end effector, and a current grip force based on the measurements. The system may further generate a composite command based on the first command and the second command to drive the at least one actuator. The system may also monitor tensioning forces on the pair of antagonistic cables and maintain a predetermined minimum tensioning force on each of the pair of antagonistic cables to prevent cable slack.

Generally, in some variations, a surgical robotic system comprises a robotic surgical tool, which includes and end effector at a distal end. The end effector comprises two opposing jaws, each manipulated by at least one actuator via a pair of antagonistic cables imparting forces when tensioned by the actuator. The system also comprises a controller having one or more processors coupled to the robotic surgical tool. The system receives a command to effect a desired state of the end effector from an input module. The desired state of the tool may include at least one of a pitch angle and a yaw angle of the end effector, and a jaw angle between the two jaws. The system then determines a desired position of the end effector based on the pitch angle and the yaw angle, and a desired grip force between the two jaws based on the jaw angle. Based on the desired position and desired grip force, the controller drives the at least one actuator to effect the desired state of the end effector.

Generally, in some variations, a system for the example robotic surgical tool control system comprises a surgical tool with an end effector having two grip members, each grip member is robotically manipulated through a pair of antagonistic cables effecting opposite pivoting of each grip member when tensioned individually. The tool control system also comprises one or more processors and an input coupled to the processors. The system receives an input jaw angle between the two grip members of the end effector. The system then determines whether the received input jaw angle indicates a desired force between the two grip members. In response to a determination that the input jaw angle indicates a desired grip force, the system generates a command for tensioning at least one of the pair of antagonistic cables for each grip member based on a difference between the desired grip force and an estimated current grip force. At least one of the pair of antagonistic cables can then be tensioned to effect the desired grip force. Otherwise if it is determined that the received input indicates a desired jaw angle, the system determines a displacement of the pair of the antagonistic cables for each grip member of the end effector, and drive the end effector via the pair of antagonistic cables to effect the desired jaw angle based on the determined displacement.

Other variations of systems and methods for controlling position and grip force of a robotic surgical tool are described herein.

BRIEF DESCRIPTION OF THE DRAWINGS

FIGS. 4A and 4B are schematic diagrams illustrating the end effector of an exemplary grasper having a robotic wrist, a pair of opposing jaws, and a pulley and cable system for coupling the robotic wrist and the pair of jaws to the actuators of a tool drive, in accordance with aspects of the subject technology.

FIG. 10 is a flowchart illustrating another example process for controlling a robotic surgical tool having an end effector with two opposing members, in accordance with aspects of the subject technology.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Overview

Disclosed is a system and method for controlling angular position and grip force of end effectors of surgical robotic arms. An end effector including a robotic wrist and one or more jaws may be coupled to actuators through metal cable or wires. The wires may work, for example, in wire pairs where pulling on one wire imparts an opposite force on the other wire of the wire pair, as such the robotic wrist may be an antagonistic robotic wrist. The control algorithm may use position and velocity feedback from the actuators, as well as force feedback from load cells on the four wires. The actuator controllers may run in the position plus current feedforward mode. The feedforward current may be provided by a grip force controller. The grip force controller may use the forces of the four wires to determine the grip force, and the grip force controller may modulate an additional current to the motors to achieve the desired grip force. Applied surgical robotic instruments includes graspers, forceps, scissors, needle drivers, retractors, pliers, and cautery instruments, among others.

Figure 1:
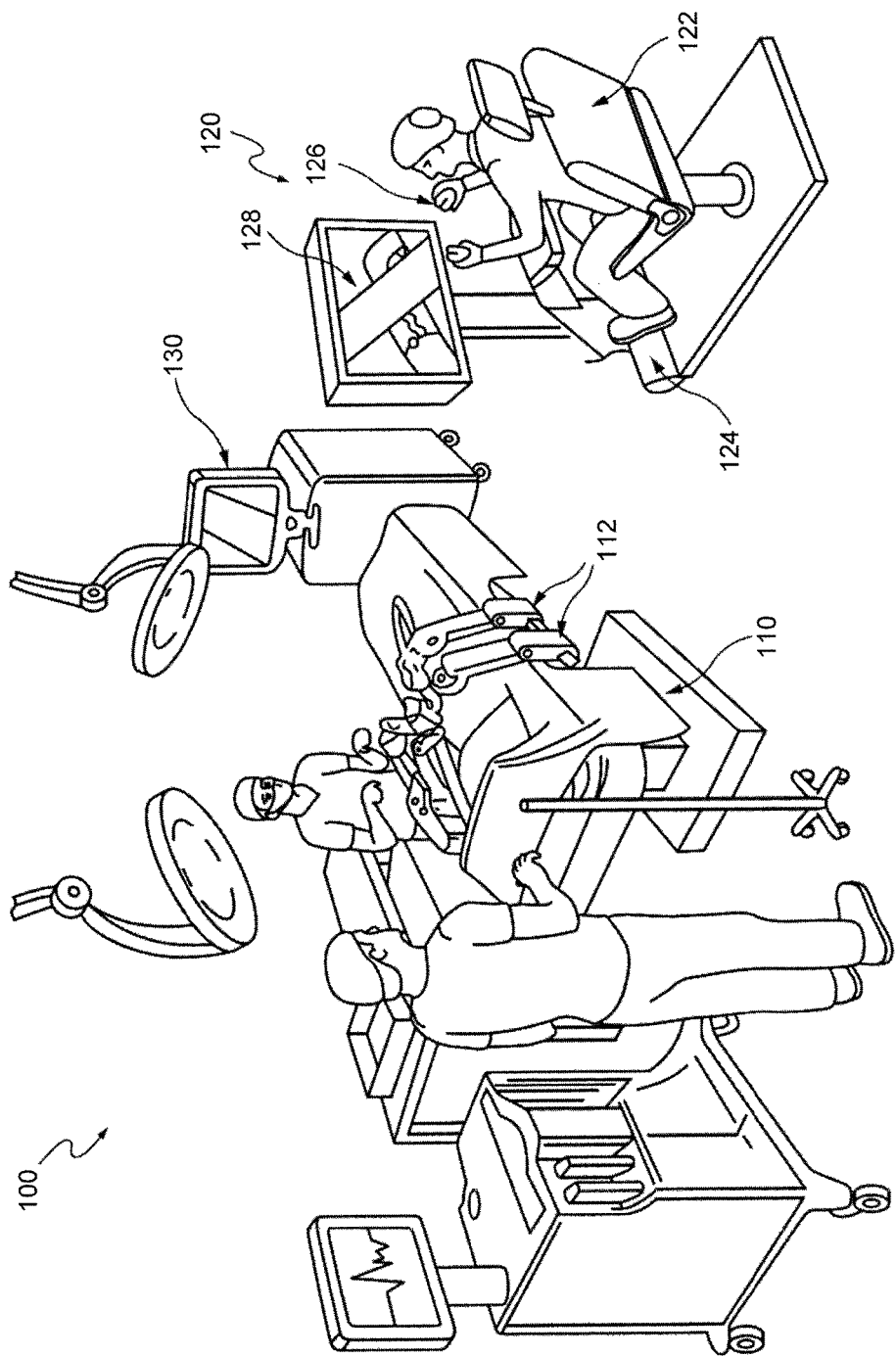
FIG. 1 is a diagram illustrating an example operating room environment with a surgical robotic system, in accordance with aspects of the subject technology.

FIG. 1 is a diagram illustrating an example operating room environment with a surgical robotic system 100, in accordance with aspects of the subject technology. As shown in FIG. 1, the surgical robotic system 100 comprises a surgeon console 120, a control tower 130, and one or more surgical robotic arms 112 located at a surgical robotic platform 110 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface.

Generally, a user, such as a surgeon or other operator, may use the user console 120 to remotely manipulate the robotic arms 112 and/or surgical instruments (e.g., tele-operation). The user console 120 may be located in the same operation room as the robotic system 100, as shown in FIG. 1. In other environments, the user console 120 may be located in an adjacent or nearby room, or tele-operated from a remote location in a different building, city, or country. The user console 120 may comprise a seat 122, foot-operated controls 124, one or more handheld user interface devices 126, and at least one user display 128 configured to display, for example, a view of the surgical site inside a patient. As shown in the exemplary user console 120, a surgeon located in the seat 122 and viewing the user display 128 may manipulate the foot-operated controls 124 and/or handheld user interface devices 126 to remotely control the robotic arms 112 and/or surgical instruments mounted to the distal ends of the arms.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 126 held in one hand) and a manual laparoscopic tool. For example, the user's left hand may be manipulating a handheld user interface device 126 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 124 and/or user interface devices 122 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Non-sterile personnel may also be present to assist the surgeon at the user console 120. When the procedure or surgery is completed, the robotic system 100 and/or user console 120 may be configured or set in a state to facilitate one or more post-operative procedures, including but not limited to, robotic system 100 cleaning and/or sterilization, and/or healthcare record entry or printout, whether electronic or hard copy, such as via the user console 120.

In some aspects, the communication between the robotic platform 110 and the user console 120 may be through the control tower 130, which may translate user commands from the user console 120 to robotic control commands and transmit to the robotic platform 110. The control tower 130 may also transmit status and feedback from the robotic platform 110 back to the user console 120. The connections between the robotic platform 110, the user console 120 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 2:
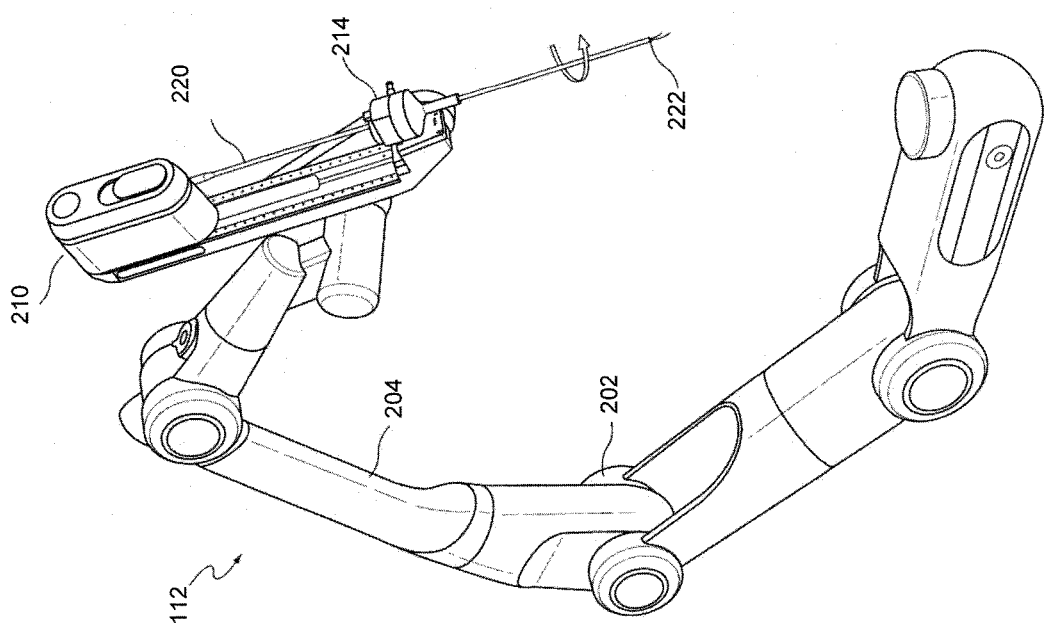
FIG. 2 is a schematic diagram illustrating one exemplary design of a robotic arm, a tool drive, and a cannula loaded with a robotic surgical tool, in accordance with aspects of the subject technology.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 112 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 112. The tool drive 210 may include a cannula 214 coupled to its end to receive and guide a surgical instrument 220 (e.g., endoscopes, staplers, etc.). The surgical instrument (or "tool") 220 may include an end effector 222 at the distal end of the tool. The plurality of the joint modules of the robotic arm 112 can be actuated to position and orient the tool drive 210, which actuates the end effector 222 for robotic surgeries.

Tool Drive and Tool

Figure 3A:
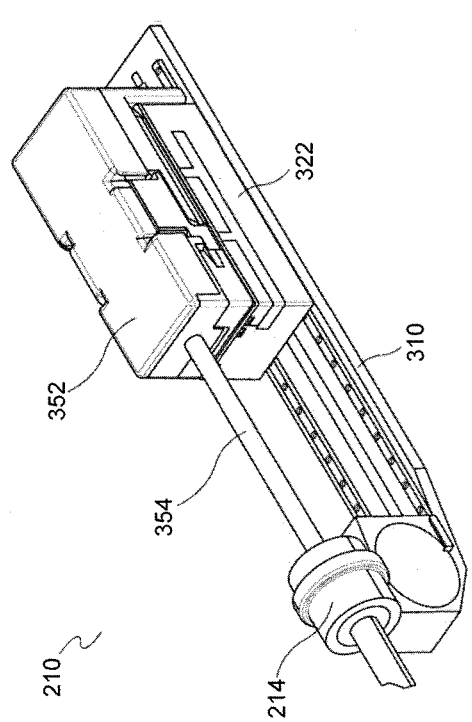
FIGS. 3A and 3B are schematic diagrams illustrating an exemplary tool drive with and without a loaded tool adjacent, respectively, in accordance with aspects of the subject technology.
Figure 3B:
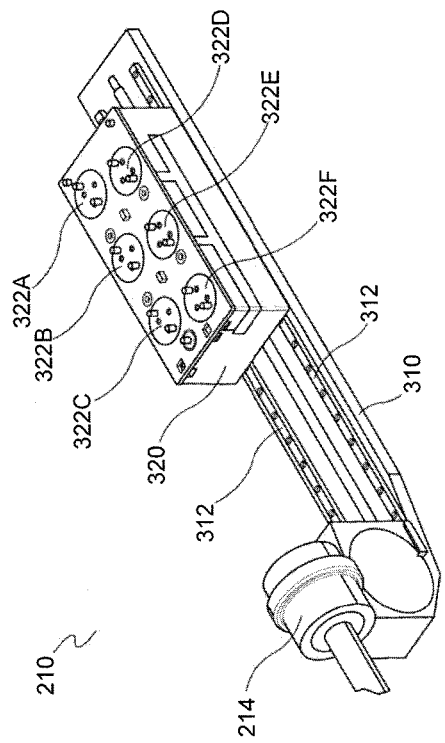

FIGS. 3A and 3B are schematic diagrams illustrating an exemplary tool drive with and without a loaded tool adjacent, respectively, in accordance with aspects of the subject technology. As shown in FIGS. 3A and 3B, in one variation, the tool drive 210 may include an elongated base (or "stage") 310 having longitudinal tracks 312 and a tool carriage 320, which is slidingly engaged with the longitudinal tracks 312. The stage 310 may be configured to couple to the distal end of a robotic arm such that articulation of the robotic arm positions and/or orients the tool drive 210 in space. Additionally, the tool carriage 320 may be configured to receive a tool base 352 of the tool 220, which may also include a tool shaft 354 extending from the tool base 352 and through the cannula 214, with the end effector 222 (not shown) disposed at the distal end.

Additionally, the tool carriage 320 may actuate a set of articulated movements of the end effector, such as through a cable system or wires manipulated and controlled by actuated drives (the terms "cable" and "wire" are used interchangeably throughout this application). The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base that are slightly staggered to reduce width of the carriage and increase the compact nature of the tool drive. As clearly shown in FIG. 3B, rotary drives 322A, 322B, and 322C may be generally arranged in a first row, while rotary drives 322D, 322E, and 322F may be generally arranged in a second row that is slightly longitudinally offset from the first row.

FIGS. 4A and 4B are schematic diagrams illustrating an end effector of an exemplary grasper 220 having a robotic wrist, a pair of opposing jaws, and a pulley and cable system for coupling the robotic wrist and the pair of jaws to actuators of a tool drive, in accordance with aspects of the subject technology. Note that although the following tool model and controller design are described with reference to the exemplary surgical robotic grasper, the proposed control system for position and grip force control may be adapted to any tools that include an end effector coupled to a tool shaft via a robotic wrist, which allows multi-axial motion (e.g., pitch and yaw) of the end effector. Similar tools include, but not limited to, graspers, grippers, forceps, needle drivers, retractors, and cautery instruments.

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 42C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The grasper 220 can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the grasper 220. In addition, the first yoke 402, the pulleys 415A and 415B, and the jaws 401A and 401B can rotate about the axis 420 to provide a pitch motion of the grasper 220. These motion of the robotic wrist and/or the jaws of the tool can be effected by controlling four independent cables 405A-405D. As shown in FIG. 4A, cable 405A may start (or terminates) from one side of the pulley 415A and route along pulleys 425A and 435A, and cable 405B is configured to terminate at the other side of the pulleys 415A and route through pulleys 425B and 435B. Similarly, another pair of cables 405C and 405D can be coupled to the jaw 401B. For example, cable 405C extends from one side of the pulley 415B to pulleys 425C and 435C; and cable 405D routes through pulleys 425D and 435D and terminates at the other side of pulley 415B. The third set of pulleys 435A, 435B, 435C and 435D are arranged in such a way as to keep the cables 405A-405D affixing to the second set of pulleys 425A-425D and prevent the cables from slipping or sliding relative to the pulleys 425A-425D.

Controlling the motions of the grasper 220 via four independent cables has several advantages. One advantage may be the reduction of the number of cables that extend from the tool base 352 to the robotic wrist compared to typical on-market designs using six cables (or three cable loops with six cable ends). Less number of cables can reduce the tool size as well as complexity of the wrist assembly, which may benefit minimally-invasive surgical procedures or non-surgical applications. Furthermore, arrangement of four independent cable instead of two or three cable loops not only allows independent control of the tension on each cable without the need for pre-tensioning of the cables, but also enables variable compliance in the wrist joints and increased sensitivity to external loads. Additionally, it is possible to readjust tension on each cable independently, which can further increase tool performance.

As shown in FIGS. 4A and 4B, the grasper 220 can be actuated to move the jaws 401A and 401B in a variety of ways such as grasping (e.g., jaws rotating independently about axis 410), yaw (e.g., jaws rotating together about axis 410), and pitch (e.g., jaws rotating about axis 420) by imparting motion to one or more of the pulleys 415A, 415B, 425A, 425B, 425C, and 425D to thereby impart motion on the first yoke 402 and/or one or both of the jaws 401A and 401B. Cables 405A-405D can be grouped into two antagonistic pairs, that is, when one cable of the antagonistic pair is actuated or tensioned, while the other cable is loosened, the jaw will rotate in one direction. Whereas when only the other cable is tensioned, the jaw will rotate in an opposite direction.

For example, cables 405A and 405B are the first antagonistic pair for moving jaw 401A, and cables 405C and 405D are the second antagonistic pair for controlling jaw 401B. When cable 405A is tensioned (e.g., by at least one of the rotary drives 322a-322f) while cable 405B is loosened, jaw 401A closes (moving towards the opposite jaw 401B). On the other hand, when cable 405B is tensioned and cable 405A is loosened, jaw 401A opens (moving away from the opposite jaw 401B). Similarly, when tensioned, cable 405C closes jaw 401B (moving towards the opposite jaw 401A) and cable 405D opens jaw 401B (moving away from the opposite jaw 401A) while the other cable loosens. As another example, grip force between the jaw 401A and jaw 401B can be achieved by continuing to tension both cable 405A and cable 405C (while cable 405B and cable 405D are loosened) after the jaws are closed (touching each other).

In case when both cables of an antagonistic pair are tensioned at the same time while both cables of the other pair are loosened, the pulley 415A or pulley 415B do not rotate. Instead, the first yoke 402 together with the jaws 401A and 401B are imparted by the pulleys 415A and 415B to pitch about the axis 420. For example, when the pair of cables 405A and 405B are both tensioned simultaneously while the pair of cable 405C and 405D are loosened, the jaws (together with the yoke 402) pitch out of the plane of the paper. Whereas when both cables 405C and 405D are tensioned simultaneously and the pair 405A and 405B are kept loose, the jaws pitch into the plane of the paper.

FIG. 4B is a schematic diagram illustrating example angle definitions for various motions of the grasper 220, in accordance with aspects of the subject technology. The angles are defined in reference to axes 410 and 420, as well as an axis 452 of the first yoke 402 and an axis 453 of the second yoke 403. For example, as shown in FIG. 4B, an angle ($\theta_1$) between axis 452 and the axis 453 may represent the rotation angle of the yoke 402 around axis 420, which may also be defined as the pitch angle ($\theta_{pitch}$) of the grasper 220 (while in FIG. 4A, the axis 452 of the yoke 402 is superimposed over the axis 453 of the yoke 403 because the jaws are staying in the reference position, i.e., no pitch motions). In addition, angles ($\theta_2$) and ($\theta_3$) can represent the angles between each of the jaws 401A and 401B and the axis 452 of the yoke 402 (as the origin), respectively. To differentiate the sides of the axis 452, angles ($\theta_2$) and ($\theta_3$) may take on different signs. For example, angle ($\theta_2$) is negative and angle ($\theta_3$) is positive, as illustrated in FIG. 4B.

In order to perform control tasks, it is often beneficial to define a consistent coordinate frame for the joint angles. For example, we may further define the jaw angle ($\theta_{jaw}$) as the angle between the two jaws 401A and 401B, and the yaw angle ($\theta_{yaw}$) as the angle between the axis 452 and the line bisecting the jaw angle. Therefore, we have:

$$\begin{cases} \theta_{pitch} = \theta_1 \\ \theta_{yaw} = \frac{1}{2}(\theta_2 + \theta_3) \\ \theta_{jaw} = \theta_2 - \theta_3 \end{cases} \quad \#(1)$$

The transformation between angles in FIG. 4B and the newly defined angles are as follows:

$$\begin{bmatrix} \theta_{pitch} \\ \theta_{yaw} \\ \theta_{jaw} \end{bmatrix} = \begin{bmatrix} 1 & 0 & 0 \\ 0 & \frac{1}{2} & \frac{1}{2} \\ 0 & 1 & -1 \end{bmatrix} \cdot \begin{bmatrix} \theta_1 \\ \theta_2 \\ \theta_3 \end{bmatrix} \quad \#(2)$$

Furthermore, the following nomenclature can be established for pulley geometries:
a) $r_{11}$ is the radius of the outer pulleys 425A and 425C on which cables 405A and 405C are residing, respectively;
b) $r_{12}$ is the radius of the inner pulleys 425B and 425D on which cables 405B and 405D are residing, respectively ($r_{11}$ may or may not be equal to $r_{12}$);
c) $r_{21}$ is the radius of pulley 415A on the side that cable 405A is residing (with reference to the center of pulley 415A and axle 412 as shown in FIG. 4A);
d) $r_{22}$ is the radius of pulley 415A on the side that cable 405B is residing (with reference to the center of pulley 415A and axle 412 as shown in FIG. 4A);
e) $r_{31}$ is the radius of pulley 415B on the side that cable 405C is residing; and
f) $r_{32}$ is the radius of pulley 415B on the side that cable 405D is residing.

While in the above example symmetrical design, $r_{31}=r_{21}$, $r_{32}=r_{22}$ and $r_{21} \neq r_{22}$ (as shown in FIG. 4A), in some other designs it is possible to have $r_{31}=r_{21}=r_{32}=r_{22}$, as wells as $r_{11}=r_{12}$.

The fundamental equation that relates cable tensions ($\xi_{[4 \times 1]}$) to joint torques ($\tau_{[3 \times 1]}$) is presented by:

$$\tau_{[3 \times 1]} = B_{[3 \times 4]} \cdot \xi_{[4 \times 1]} \quad \#(3)$$

where matrix (B) has the following form:

$$B = \begin{bmatrix} -r_{11} & -r_{12} & r_{11} & r_{12} \\ -r_{21} & r_{22} & 0 & 0 \\ 0 & 0 & r_{31} & -r_{32} \end{bmatrix} \quad \#(4)$$

and ($\xi_1, \xi_2, \xi_3, \xi_4$) corresponds to cable tensions on cables 405A, 405B, 405C and 405D, respectively.

$$\xi_{[4 \times 1]} = [\xi_1 \xi_2 \xi_3 \xi_4]^T \quad \#(5)$$

In Eq. (1), ($\tau_{[3 \times 1]}$) is the vector of virtual joint torques applied by the cables, which may cause the joints overcome friction and move against the external forces. Vector ($\tau_{[3 \times 1]}$) has three components:

$$\tau_{[3 \times 1]} = [\tau_1 \tau_2 \tau_3]^T \quad \#(6)$$

where ($\tau_1$) is the pitch joint torque, and ($\tau_2$) and ($\tau_3$) are the joint torques of jaw 401A and jaw 401B, respectively.

The kinematic relationship that relates the ideal cable displacements (assuming no cable elasticity) and jaw angles are as follows:

$$q_{[4 \times 1]}[q_1 q_2 q_3 q_4]^T = B^T \cdot \theta_{[3 \times 1]} \quad \#(7)$$

where ($q_{[4 \times 1]}$) is the four-element vector containing the ideal displacements of cables 405A-405D, and ($\theta_{[3 \times 1]}$) is the vector of angles illustrated in FIG. 4B:

$$\theta_{[3 \times 1]} = [\theta_1 \theta_2 \theta_3]^T \quad \#(8)$$

In the actual case, where the cables are elastic, the actual and ideal cable displacements are related as follows:

$$\xi_{[4 \times 1]} k_e (x_{[4 \times 1]} - B^T \cdot \theta_{[3 \times 1]}) \quad \#(9)$$

where $k_e$ is the elastic constant of the cables in N/m (assuming all cables are similar).

Control System Design

Described below is a method and system for controlling angular position and grip force of a distal end effector of a robotic surgical instrument. The end effector may include a robotic wrist and a pair of opposing members (e.g., jaws or claws), each being movable between an open position and a closed position actuated by two antagonistic wires. A total of four wires may each be driven by an independent actuator or motor, as illustrated in FIGS. 3 and 4 and described in the corresponding sections. The control system may include feedback loops involving position and velocity feedback from the actuators and force feedback measured on the four wires, to effect desired position and grip force. In some implementations, the actuator controllers may be running a position plus feedforward current mode. For example, a position controller may drive the distal end effector to the desired angular position in space based on the positional feedback, while a grip force controller provides additional feedforward current based on the grip force measured by load cells on the four wires to achieve the desired grip force between the opposing members.

Figure 5A:
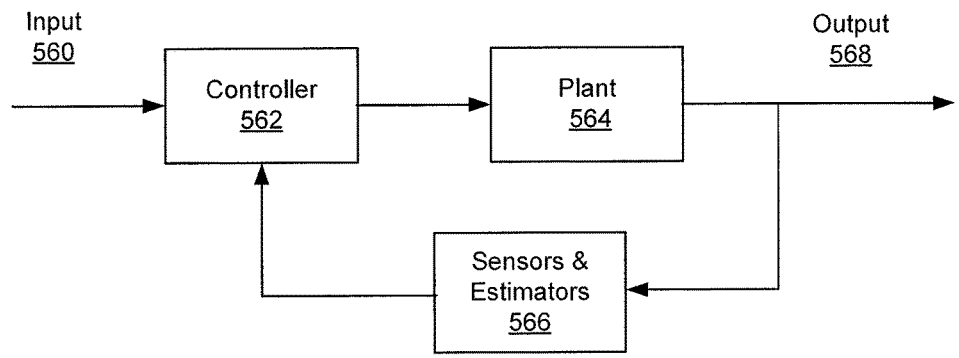
FIGS. 5A and 5B are block diagrams illustrating an exemplary control system for controlling the position and grip force of an end effector of a robotic surgical tool, in accordance with aspects of the subject technology.

FIG. 5A is a block diagram illustrating a high-level control system for controlling a surgical tool, in accordance with aspects of the subject technology. The control system comprises an input 560, a controller 562, a plant 564, an output 568, and sensors and estimators 566 on a feedback path between the output 568 and the controller 562. The plant 564 may include tool actuators and end effector (e.g., actuator units 510 and cable and wrist links 512 in FIG. 5B). The controller 562 may include one or more processors configured by software instructions stored on a memory to calculate motions of the plant 564 in response to the input 560, which may indicates a desired movement of the surgical tool's end effector. Commands thus generated by the controller 562 may drive the tool actuators to facilitate the desired movement of the end effector. The output 568, such as position, velocity, cable tension, and grip force of the end effector, may be directly measured or estimated by the sensors and estimators 566 and fed back to the controller 562 for closed-loop control.

Figure 5B:
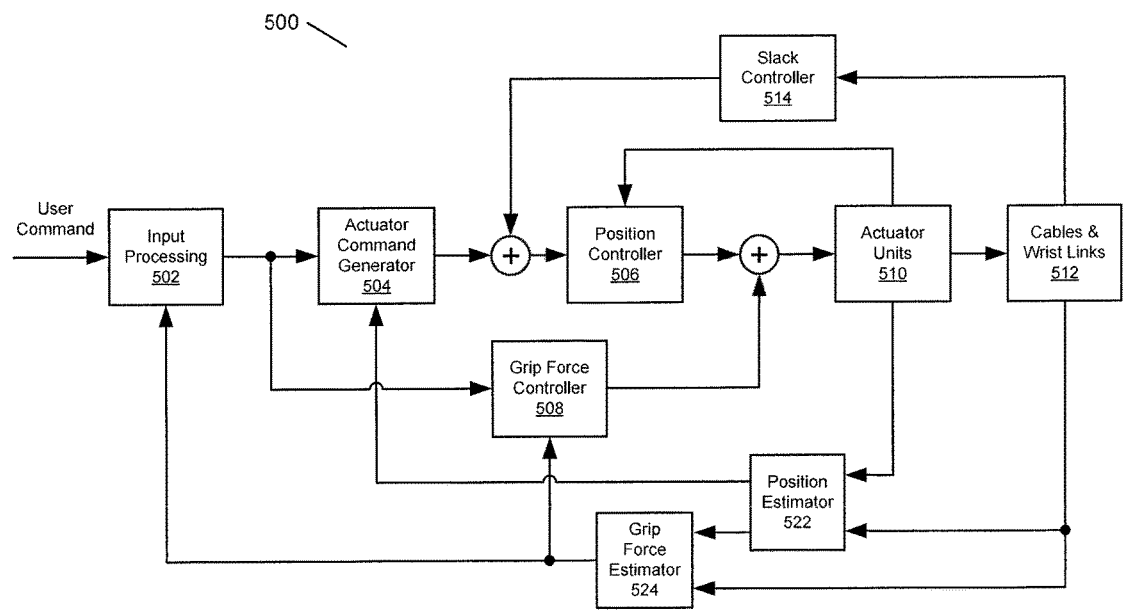

FIG. 5B is a block diagram illustrating an exemplary control system 500 for controlling the position and grip force of an end effector of a robotic surgical tool, in accordance with aspects of the subject technology. The robotic control system 500 comprises an input processing unit 502, a actuator command generator 504, a position controller 506, a grip force controller 508, a plant including one or more actuator units 510 and/or cables and wrist links 512, a slack controller 514, a position estimator 522 and a grip force estimator 524. Note that additional, different or fewer components than shown in the figure may be used. Variations in the arrangement and types of the components may also be made without departing from the spirit or scope of the claims as set forth herein.

The input processing unit 502 and the actuator command generator 504 receive desired angular positions of the end effector and translate the desired angular positions into corresponding actuator position commands (via inverse kinematics algorithm) and/or grip force command, which are output to the position controller 506 and/or grip force controller 508. For example, the input desired angular positions may include pitch angle ($\theta_{pitch}$), yaw angle ($\theta_{yaw}$), and jaw angle ($\theta_{jaw}$). The desired jaw angle input may be treated as position control command when the angle is no less than a threshold. The threshold corresponds to an angle at which both jaws are just simultaneously in contact with the object(s) in between. In case there is no objects to grasp, the threshold is zero degree when the jaws begin to touch each other. For any desired jaw angle less than the threshold, the input may be translated to a desired grip force command and forwarded to the grip force controller 508, which can generate a current command in addition to the position commands to achieve the desired grip force.

Figure 6:
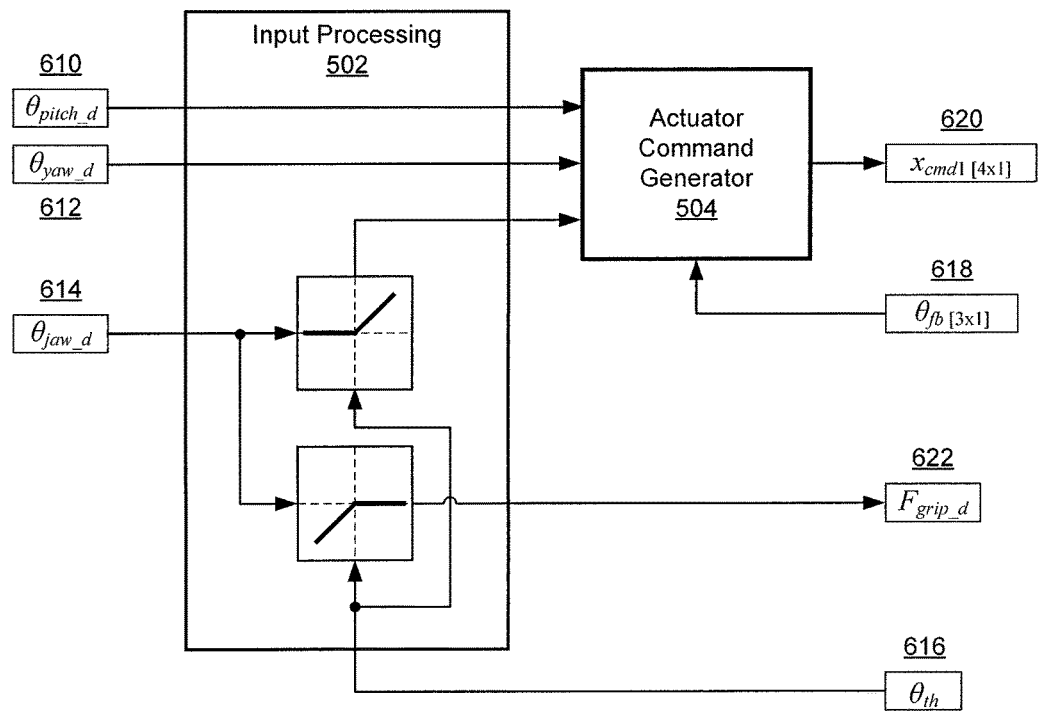
FIG. 6 is a block diagram illustrating an exemplary input processing module of a robotic surgical tool control system, in accordance with aspects of the subject technology.

FIG. 6 is a block diagram illustrating an exemplary design for the input processing unit 502 and actuator command generator 504 of a robotic surgical tool control system, in accordance with aspects of the subject technology. In some implementations, the desired pitch angle ($\theta_{pitch\_d}$) 610 and the desired yaw angle ($\theta_{yaw\_d}$) 612 are always treated as desired position of the end effector and passed to the actuator command generator 504 directly as input. Whereas the desired jaw angle ($\theta_{jaw\_d}$) 614 is first compared by the input processing unit 502 against a threshold value ($\theta_{th}$) 616 to determine whether the input is a desired position or a desired force command for the end effectors. The threshold ($\theta_{th}$) 616 provided to the input processing unit 502 can be a predetermined value or dynamically determined (e.g., by the grip force estimator 524). Details on how to determine the threshold will be further explained below.

For example, if the desired jaw angle ($\theta_{jaw\_d}$) 614 is below the threshold ($\theta_{th}$) 616 as determined by the input processing unit 502, the desired jaw angle ($\theta_{jaw\_d}$) 614 is interpreted as a grip force command and the angle value is converted to a desired grip force ($F_{grip\_d}$) 622 and output to the grip force controller 508. The desired grip force may be determined based on a function of the desired jaw angle ($\theta_{jaw\_d}$) 614 and/or the threshold ($\theta_{th}$) 616. The function may be a linear function, an exponential function, a quadratic function, or any other proper functions. On the other hand, if the desired jaw angle ($\theta_{jaw\_d}$) 614 is above the threshold ($\theta_{th}$) 616, it is interpreted as a position command and passed to the actuator command generator 504 as a position input together, with the desired pitch angle ($\theta_{pitch\_d}$) 610 and the desired jaw angle ($\theta_{yaw\_d}$) 612.

Subsequently, the actuator command generator 504 uses inverse kinematics to generate a position command ($x_{cmd1}$) 620 for the position controller 506 to actuate the end effector. The actuator command generator 504 may also receive a feedback angular position ($\theta_{fb}$) 618 (e.g. from the position estimator 522) to adjust the generated position command ($x_{cmd1}$) 620 based on the feedback (e.g., to compensate for cable elasticity).

Referring back now to FIG. 5B. The position controller 506 may receive position feedback from position and/or speed sensors on the actuator units 510. Achieving the desired actuator positions can in turn lead to the desired position of the robotic wrist due to the kinematic relationship between the actuators and the robotic wrist. Hence, it is preferred that controllers of non-zero steady-state error type are employed in the position controller 506, as controllers of zero steady-state type may "fight" the grip force controller by forcing the exact positions (thus saturating the current command in the process) while making the desired grip force hard to achieve. Examples of the preferred non-zero steady-state error controllers include the proportional plus derivative (PD) controllers. A PD controller allows for compliance of the grasper jaws necessary for a grip force controller to generate the desired grip force. The grip force controller 508 may then be the main factor in dominating the compliance in the degree of freedom of jaw closure during grip force control (as opposed to the position controller 506).

Since the actuator units 510 are coupled to the robotic wrist through elastic cables (or wires), which may change length under force, estimation only based on a pure kinematic relation between actuator positions and wrist movements may not be accurate. The position estimator 522 may provide the actuator command generator 504 and the grip force estimator 524 with a more accurate estimate of the wrist joint positions and velocities by taking into account the cable elasticity in estimation algorithms (e.g., using a Kalman filter). The estimated position and velocity information can then be used for accurate positioning of the wrist, as well as estimation of the friction.

In some implementations, the grip force controller 508 takes feedback of cable tensions measured by load cells or torque sensors on the cable wires. Algorithms can then be used by the grip force estimator 524 to estimate the grip force between the jaws based on the tension values measured on the cables. The grip force controller 508 may compare the estimated value to the desired grip force and generates additional current commands to achieve the desired grip force. Alternatively, instead of the measurements from the force/torque sensing load cells, the grip force controller 508 can use motor currents as feedback, combined with some estimation techniques, to produce the additional current command for grip force generation.

As described above, the end effector may be coupled to the tool drive through four independent cables, each of which is actuated by an independent motor. In particular, the end effector may include a robotic wrist and a pair of opposing jaw members, each jaw being movable between an open position and a closed position. In some implementations, the motors may be driven by current. The current command may include two parts: the first part of the driving current may be from the joint angle controller 506 and the second part from the grip force controller 508. The two current commands may be summed up and sent to the actuator units 510.

Figure 7:
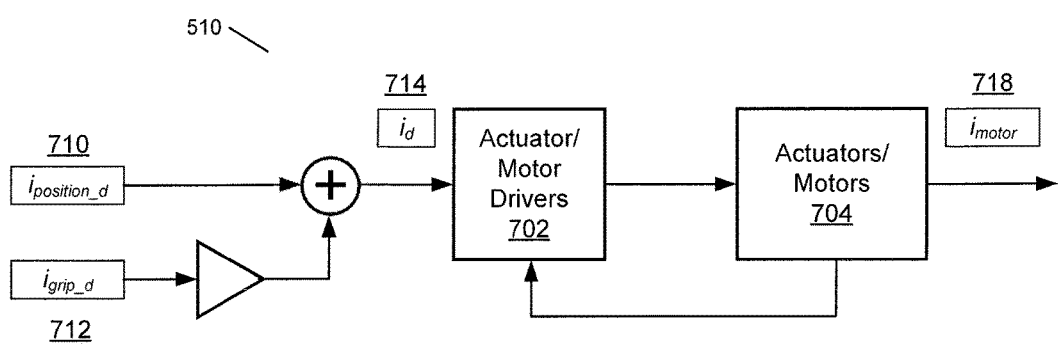
FIG. 7 is a block diagram illustrating an exemplary grip controller module of a robotic surgical tool control system, in accordance with aspects of the subject technology.

FIG. 7 is a block diagram illustrating exemplary actuator units 510 of a robotic surgical tool control system and input/output thereof, in accordance with aspects of the subject technology. The actuator units may include one or more low level actuators or motor drivers 702, each driving a corresponding actuator or motor 704. Note that additional, different or fewer components may be used in the actuator units. In some implementations, the actuators or motors 704 are electric current driven DC motors. The low level actuator or motor drivers 702 receive input current command ($i_d$) 714, which is a sum of a desired current command ($i_{position\_d}$) 710 from the position controller 506 and a desired current command ($i_{grip\_d}$) 712 from the grip force controller 508. The actuator or motor drivers 702 may then drive the actuators or motors 704, which in turn drive the end effector with the output current ($i_{motor}$) 718. The status of the motors 704, e.g., current ($i_{motor}$) 718, may be fed back to the motor drivers 702. By summing up the desired current commands ($i_{position\_d}$) 710 and ($i_{grip\_d}$) 712, the actuators units 510 may drive the one or more motors to effect desired movement and/or grip force of the end effector.

Due to the antagonistic nature of the robotic wrist, the desired grip force command ($i_{grip\_d}$) 712 for different motors may be antagonistic, for example, positive for closing actuators and negative for opening actuators. It may be advantageous that the additional current commands be added to the existing current command for closing the jaws at the two closing actuators and subtracted from the current commands for opening the jaws to the two opening actuators. In other implementations, the additional current command can be sent only to the two closing actuators for controlling the closing cables, which may result in a reduced performance. In the latter scenario, the threshold ($\theta_{th}$) 616 at which the input jaw angle, e.g., desired jaw angle ($\theta_{jaw\_d}$) 614, is used to control the grip force may become critical, i.e., the threshold need to be set at the exact angle of contact. Otherwise, the opening cables may resists more as the jaws get closer while increasing the grip force. It may reach the point where the closure of grip becomes impossible due to saturation of actuators and cable forces. Therefore, a separate estimator may be needed to estimate friction and to estimate the contact angle, so that the threshold can be determined and provided to the input processing unit 502.

Alternatively, the grip force controller 508 may use a model to calculate the additional current needed for generating the desired grip force. Furthermore, instead of generating additional current setpoints to be added and/or subtracted from the current command generated by the position controller 506, the grip force controller 508 may provide additional position setpoints to be added to the two closing cables position setpoints and subtracted from the two opening cables position setpoints (a setpoint is simply the desired or target value for an essential variable of a system, such as a desired angular position).

Referring back to FIG. 5B, the slack controller 514 may perform the task of ensuring the tensions on the cables never falls below zero (or a predetermined positive value to compensate slackness). Cables are tension-only members of the end effector, to which negative forces cannot be applied. Besides, when cables become slack, the kinematic relation between the two ends of the cable no longer holds. Therefore, it is desirable to prevent the tensions on the cables from dropping to zero under any circumstances. To achieve this goal, the slack controller 514 may monitor the force values from load cells on the cables and compare the minimum of the force values to a predetermined threshold. If the minimum force value across all the cables falls below the threshold, the slack controller 514 may generate an additional position command to all the actuators to ensure that the desired minimum tension is maintained. These additional position commands need to bin in the null space of the wrist cable system, so as not to change the grip force or cause any unwanted motions to the wrist. Alternatively, instead of additional position command, the slack controller may provide additional currents to the actuators with magnitudes in the null space of the wrist cable system (assuming identical actuators). In either case, zero steady-state type controllers, such as a proportional plus integral (PI) controller, can be deployed as the slack controller 514 to maintain the desired minimum force on the cables.

The following paragraphs describe an example control algorithm in more details regarding the input, output and functions of each component in an example control system. The proposed methodology may rely on using position plus feed forward current control on the actuators driving the end effector. The position controller may drive the end effector to the desired position setpoints in space through the cables, while additional feed forward current may be added to effect the desired grip force in between the two end effector members.

Figure 8A:
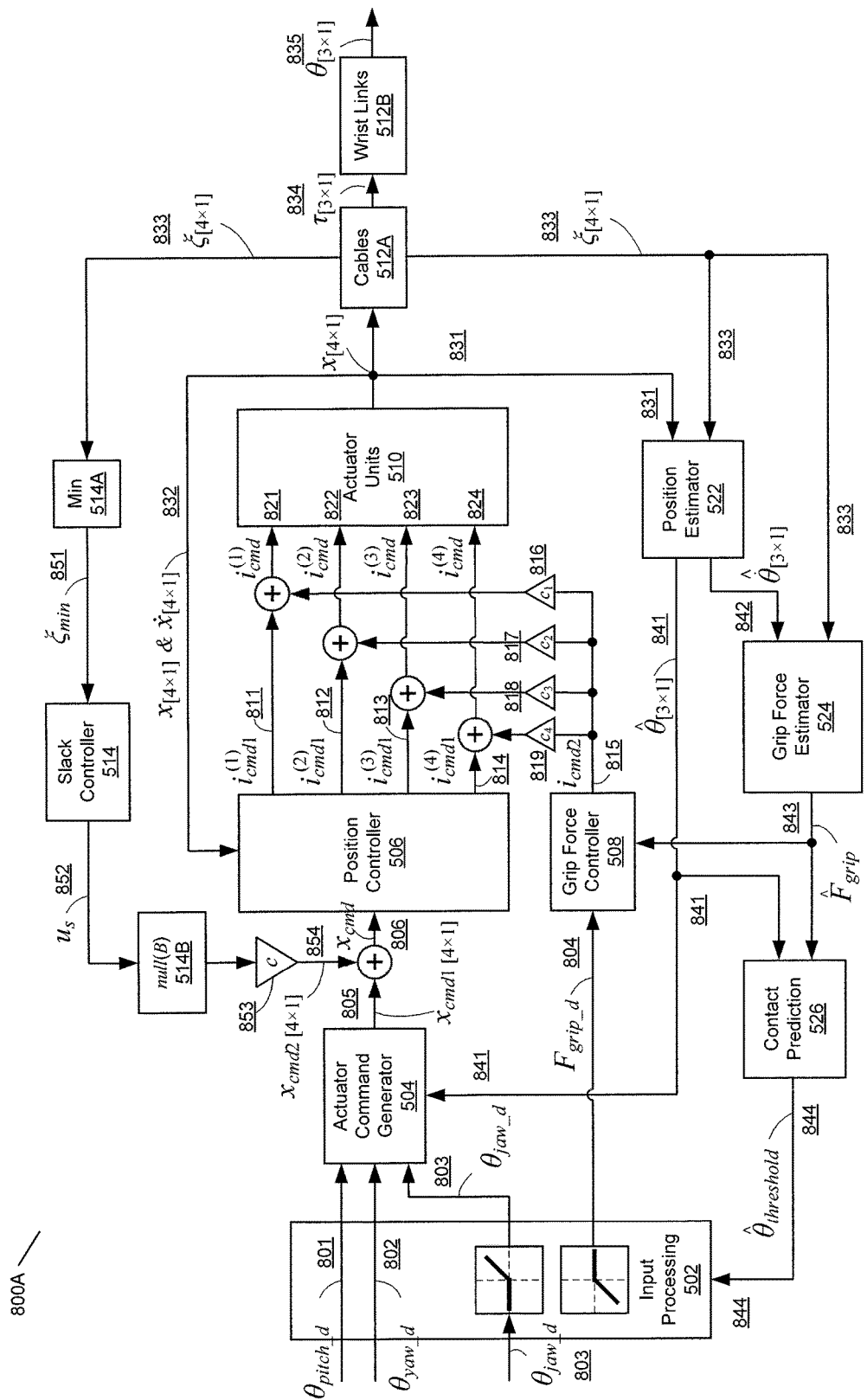
FIGS. 8A and 8B are detailed block diagrams illustrating an exemplary control system for controlling the position and grip force of an end effector of a robotic surgical tool, in accordance with aspects of the subject technology.

Now referring to FIG. 8A, a detailed block diagram illustrating an exemplary control system 800A for controlling the position and grip force of an end effector of a robotic surgical tool, in accordance with aspects of the subject technology. Note that the description is not intended to limit the control systems to the specific implementation, but rather to enable a person skilled in the art to make and use this invention. Furthermore, the control systems and methods may include more or fewer components. Each of these components may be used with one another, or may be used individually for various purposes. For instance, similar to the example control system 500, the control system 800A comprises a input processing unit 502, a actuator command generator 504, a position controller 506, a grip force controller 508, a slack controller 514, a position estimator 522, a grip force estimator 524, and four actuator units (motors and drivers) 510. In the control system 800A, cables 512A and wrist links 512B are separated, and a contact prediction unit 526 is added to the control system 500 (as shown in FIG. 5B).

The control system 800A may take input of desired angles 801, 802 and 803. Among the three input angles, the desired pitch angle ($\theta_{pitch\_d}$) 801 and the desired jaw angle ($\theta_{yaw\_d}$) 802 are directly passed to the actuator command generator 504. The desired jaw angle ($\theta_{jaw\_d}$) 803 is provided to the input processing unit 502 to be compared against a threshold value ($\hat{\theta}_{threshold}$) 844, which may be estimated by the contact prediction unit 526.

As described above, the input pitch angle 801 (rotation about axis 420 in FIG. 4B) and yaw angles 802 (angle between axis 452 and the middle point of jaws, as shown in FIG. 4B) of the end effector can be controlled in position mode by the position controller 506. The input jaw angle (angle between the two jaw members) may be interpreted differently depending on whether the desired jaw angle 803 is smaller or greater than the threshold value 844. When the desired jaw angle 803 is below the threshold 844 as determined by the input processing unit 502, a desired grip force ($F_{grip\_d}$) 804 is generated for the grip force controller 508. The desired grip force may be determined according to a function of the desired jaw angle 803 and/or the threshold 844. The function may be a linear function, an exponential function, a quadratic function, or other functions. The desired jaw angle 803 may be passed to the actuator command generator 504 as part of the position command regardless of the comparison result, however, it is treated as a position command only when it is greater than the threshold 844.

The threshold 844 corresponds to an angle value at which the two members of the jaws are just in contact with each other or any objects being grasped in between. In other words, the input jaw angle is switched from an angular position command to a grip force command at the threshold value. The threshold 844 can be a predetermined value (e.g., zero degree). Preferably, the threshold is determined in real time by estimating the actual jaw angle at which contact with grasped objects first occurs. For example, the contact prediction unit 526 may detect and/or predict the instance a contact happens based on estimations of the jaw angles and the grip force value, so as to determine the threshold. The determined threshold is then passed on to the input processing unit 502 for interpreting the input jaw angle. The output of the actuator command generator 504 may include displacement command ($x_{cmd}$) 806 for the position controller 506 to produce four cable displacements, which may in turn be applied to the four actuator units (or motors) 510.

By representing the desired angles with $[\theta_{pitch\_d} \; \theta_{yaw\_d} \; \theta_{jaw\_d}]^T$, we can convert the vector to the desired angles $\theta_{d[3\times1]}$ in the joint space using Eq. (2):

$$\theta_{d[3\times1]} = \begin{bmatrix} \theta_{1\_d} \\ \theta_{2\_d} \\ \theta_{3\_d} \end{bmatrix} = \begin{bmatrix} 1 & 0 & 0 \\ 0 & \frac{1}{2} & \frac{1}{2} \\ 0 & 1 & -1 \end{bmatrix}^{-1} \cdot \begin{bmatrix} \theta_{pitch\_d} \\ \theta_{yaw\_d} \\ \theta_{jaw\_d} \end{bmatrix} \qquad \#(10)$$

where the subscript "_d" denotes the desired value for the corresponding input as well as converted parameters. In case a grip force is desired, the jaw angle input may be converted to the desired grip force ($F_{grip\_d}$) 804 and sent to the grip force controller 508.

The actuator command generator 504 may receive a feedback from the position estimator 522 on estimations of the joint angles ($\hat{\theta}_{[3\times1]}$) 841. A first order estimate of joint angles can be gauged from measurement of actuator (motor) positions ($x_{[4\times1]}$) 831 and the cable tensions ($\xi_{[4\times1]}$) 833 using Eq. (7):

$$\hat{\theta}_{[3\times1]} = B^T(x_{[4\times1]} - k_e^{-1}\xi_{[4\times1]}) \qquad \#(11)$$

where $k_e$ is the elastic constant of the cables in the unit of N/m, the cable tensions ($\xi_{[4\times1]}$) 833 is defined in Eq. (3), and ($x_{[4\times1]}$) 831 is a vector of position sensor measurement on the actuator units 510:

$$x_{[4\times1]} = [x_1 x_2 x_3 x_4]^T \qquad \#(12)$$

In some implementations, the control system 800A may adopt a closed-loop control to achieve the desired joint positions (pitch and yaw). In the closed-loop control scheme, the actuator command generator 504 may keep monitoring the angular position from the position estimator 522 and modulate its position command ($x_{cmd1}$) 805 until the desired joint angles are achieved. Alternatively, the actuator command generator 504 may perform open-loop control and use an inverse kinematic technique based on Eq. (5) to obtain the desired displacement of the four motors:

$$x_{cmd1[4\times1]}q_{d[4\times1]}=B^T\theta_{d[3\times1]} \qquad \#\#(13a)$$

where B and $\theta_{d[3\times1]}$ are defined in Eq. (4) and Eq. (10), respectively. To account for the effect of cable elasticity, the desired displacement of the four motors can be further improved using Eq. (9):

$$x_{cmd1[4\times1]}=B^T\theta_{d[3\times1]}+k_e^{-1}\xi_{[4\times1]} \qquad \#\#(13b)$$

Furthermore, as shown in FIG. 8, the position setpoint or command ($x_{cmd}$) 806 may be the sum of two components:

$$x_{cmd[4\times1]}=x_{cmd1[4\times1]}+x_{cmd2[4\times1]} \qquad \#(14)$$

where the first component ($x_{cmd1}$) 805 may be generated by the actuator command generator 504 outlined above, and a second component ($x_{cmd2}$) may be provided by the slack controller 514.

The second displacement command ($x_{cmd2}$) 854 may be generated by the slack controller 514 based on the cable tensions ($\xi_{[4\times1]}$) 833 feedback (e.g., from load cells on the four cables 512A). A minimum tension value ($\xi_{min}$) 851 among the cable tension feedback ($\xi_{[4\times1]}$) 833 is first determined by a "min" unit 514A:

$$\xi_{min}=(\xi_1,\xi_2,\xi_3,\xi_4) \qquad \#(15)$$

Next, the slack controller may compare the minimum value ($\xi_{min}$) 851 to a desired minimum tension value ($\xi_{min\_d}$) to generate an additional displacement command ($u_s$) 852. A zero steady-state error type controller may be adopted for the purpose of maintaining the minimum desired tension on all four cables. Such controllers, in discrete domain, may take the following form (other forms, such as state-space, or nonlinear, are also possible):

$$C(z)=\frac{b_m z^m+b_{m-1}z^{m-1}+\ldots+b_1 z^1+b_0}{(z-1)^p(a_n z^n+a_{n-1}z^{n-1}+\ldots+a_1 z^1+a_0)} \qquad \#(16a)$$

where C(z) is the controller transfer function from input ($\xi_{min}$) 851 to output ($u_s$) 852, and z is the z-transform parameter. Furthermore, parameters $a_i$ and $b_i$ are real numbers such that the corresponding polynomials in the numerator and denominator of C(z) have roots strictly inside the unit circle, and no roots at z=+1. Parameters m, n, and p are integers such that p>0 and m≤n+p to ensure the controller transfer function C(z) proper.

A proportional plus integral (PI) controller is a special case of C(z) and may be used to regulate the minimum tension in the four cables as described above and may take the following form in the time domain:

$$u_s=-k_{ps}(\xi_{min}-\xi_{min\_d})-k_{is}\int(\xi_{min}-\xi_{min\_d})dt \qquad \#(16b)$$

where $k_{ps}$ and $k_{is}$ are the proportional and integral gains, respectively.

In order to regulate the tension on the cables to keep the minimum tension and not to disturb the joint angle positions or the grip force, the position command ($x_{cmd2}$) 854 needs to be in the null space of the wrist cable system. To achieve this, the scalar displacement ($u_s$) 852 may be further multiplied by the null space of the matrix (B). Hence, the second displacement command ($x_{cmd2}$) 854 may take the following form:

$$x_{cmd2[4\times1]}=c\cdot u_s\cdot\text{null}(B) \qquad \#(17)$$

where (c) 853 is a constant to scale the null space vector so that its element corresponding to the cable with minimum tension equals to unity (i.e., one).

Alternatively, the slack controller 514 may generate commands including additional currents directly to drive the actuators 510 (with magnitudes in the null space of the wrist cable system), instead of the additional position command ($x_{cmd2}$) 854 provided to the position controller 506. In such an implementation, the additional current commands may be added to each of the ($i_{cmd}$) components 821-824.

The position controller 506 may be used to achieve desired actuator positions which in turn may result in the desired position of the wrist through a kinematic relationship. To regulate the current command sent to each motor, the position controller 506 may rely on feedback from actuators' position and/or speed sensors or velocity estimates. Furthermore, each of the motors 510 may receive its current setpoints or commands from the position controller 506 combined with additional or less current, which depends on each value ($c_i$) 816-819 in a scaling vector ($c_{i[4\times1]}=[c_1\ c_2\ c_3\ c_4]^T$) from the grip force controller 508.

$$i_{cmd[4\times1]}[i_{cmd}^{(1)}i_{cmd}^{(2)}i_{cmd}^{(3)}i_{cmd}^{(4)}]^T=i_{cmd1[4\times1]}+c_{i[4\times1]}\cdot i_{cmd2} \qquad \#(18)$$

The position controller 506 may generate current commands ($i_{cmd1[4\times1]}$) based on the position setpoint or command ($x_{cmd}$) 806, as well as position ($x_{[4\times1]}$) and velocity ($\dot{x}_{[4\times1]}$) 832 feedback. Preferably, the position controller 506 may be implemented with a nonzero steady-state-error controllers, as discussed above. Such controllers, in discrete domain, may take the following form (other forms, such as state-space, or nonlinear, are also possible):

$$C(z)=\frac{b_m z^m+b_{m-1}z^{m-1}+\ldots+b_1 z^1+b_0}{a_n z^n+a_{n-1}z^{n-1}+\ldots+a_1 z^1+a_0} \qquad \#(19a)$$

where C(z) is the controller transfer function between input ($x_{cmd}$) 806 and output ($i_{cmd1}$) 811-814, and z is the z-transform parameter. Furthermore, parameters $a_i$ and $b_i$ are real numbers such that the corresponding polynomials in the numerator and denominator of C(z) have roots strictly inside the unit circle, and no roots at z=+1. Parameters m and n are integers such that (m≤n) to ensure the controller transfer function C(z) proper.

A proportional plus derivative (PD) controller is a special case of C(z) in Eq. (19a) and may be used for generating the current commands ($i_{cmd1}$) 811-814. Thus the first component of the current command to the four actuators, as shown in Eq. (19b), can be generated as follows (expressed in the time domain):

$$i_{cmd[4\times1]}[i_{cmd}^{(1)}i_{cmd}^{(2)}i_{cmd}^{(3)}i_{cmd}^{(4)}]^T=-k_p(x_{[4\times1]}-x_{cmd[4\times1]})-k_d\dot{x}_{[4\times1]} \qquad \#(19b)$$

where ($k_p$) and ($k_d$) are controller gains, ($x_{[4\times1]}$) 831 is a 4-tuple vector of the actuator positions defined in Eq. (12), and ($\dot{x}_{[4\times1]}$) is a 4-tuple vector of actuator velocities, which can be direct speed sensor measurement or estimates from the position derivatives.

The grip force controller 508 may generate a second current a ($i_{cmd2[4\times1]}$) 815 which can be combined with the current command ($i_{cmd1[4\times1]}$) from the position controller 506 for each of the actuators 510 to effect the grip force. The second current command ($i_{cmd2[4\times1]}$) 815 may be generated by the grip force controller 508 based on the desired grip force input ($F_{grip\_d}$) 804, as well as grip force feedback ($\hat{F}_{grip}$) 843 provided by the grip force estimator 524.

Assuming L defines the length of the jaw from jaw rotation axis to the point of grip load application, the grip force between the two jaw members may be estimated using the following equation:

$$\hat{F}_{grip} = \frac{\tau_2 - \tau_3}{2L} \qquad \#(20)$$

where ($\tau_2$) and ($\tau_3$) are the joint torques of the two jaw elements from Eq. (1). Substituting with the joint torques from Eq. (3) and using Eq. (4), we may obtain:

$$\hat{F}_{grip} = \frac{-r_{21}\xi_1 + r_{22}\xi_2 - r_{31}\xi_3 + r_{32}\xi_4}{2L} \qquad \#(21)$$

Note that Eq. (21) assumes that the cable forces are measured directly using load cells or torque sensors on the cables 512A. Cable force values may also be estimated indirectly using motor currents and motor states, such as ($x_{[4\times1]}$ & $\dot{x}_{[4\times1]}$) 832 in conjunction with advanced estimation algorithms (e.g., using a Kalman filter).

Once the grip force estimate ($\hat{F}_{grip}$) 843 is obtained, the grip force controller 508 may then compare the value to the desired grip force value ($F_{grip\_d}$) 804 and generate the second current command ($i_{cmd2}$) 815 to achieve the desired grip force. A zero steady-state error type controller similar to the one shown in Eq. (16a) may be adopted for the purpose of controlling the grip force. In this case, C(z) will be the controller transfer function between the input ($F_{grip\_d}$) 804 and output ($i_{cmd2}$) 815. A special case of C(z) includes a proportional plus integral (PI) controller, which may be used for regulating the grip force and may take the following form in time domain:

$$i_{cmd2} k_{pg}(\hat{F}_{grip} - F_{grip\_d}) k_{ig} \int (\hat{F}_{grip} - F_{grip\_d}) dt \qquad \#(22)$$

where $k_{pg}$ and $k_{ig}$ are the proportional and integral gains, respectively.

As such, the scalar second current command ($i_{cmd2}$) 815 may pass through individual gain amplifiers 816-819 to produce a scaled current command, which may be added to current command ($i_{cmd1[4\times1]}$) 811-814, respectively. Each component ($i_{cmd}^{(1)} i_{cmd}^{(2)} i_{cmd}^{(3)} i_{cmd}^{(4)}$) 821-824 of the combined current command ($i_{cmd}$) may then be applied to the actuators or motors 510. For example, the second current command ($i_{cmd2}$) 815 may be added to the current command of the two actuators closing the jaws and may be subtracted from the current commands to the two actuators opening the jaws. Different values may be chosen for each component ($c_i$) 816-819 in the scaling vector ($c_{i[4\times1]}$) depending on implementations. The following equations demonstrate various example current command settings for the four motors, which may result in varied performance:

$$\begin{cases} i_{cmd}^{(1)} = i_{cmd1}^{(1)} + i_{cmd2} \\ i_{cmd}^{(2)} = i_{cmd1}^{(2)} - \left(\frac{r_{22}}{r_{21}}\right) i_{cmd2} \\ i_{cmd}^{(3)} = i_{cmd1}^{(3)} + i_{cmd2} \\ i_{cmd}^{(4)} = i_{cmd1}^{(4)} - \left(\frac{r_{32}}{r_{31}}\right) i_{cmd2} \end{cases} \qquad \#(23)$$

$$\begin{cases} i_{cmd}^{(1)} = i_{cmd1}^{(1)} + r_{21} i_{cmd2} \\ i_{cmd}^{(2)} = i_{cmd1}^{(2)} - r_{22} i_{cmd2} \\ i_{cmd}^{(3)} = i_{cmd1}^{(3)} + r_{31} i_{cmd2} \\ i_{cmd}^{(4)} = i_{cmd1}^{(4)} - r_{32} i_{cmd2} \end{cases} \qquad \#(24)$$

$$\begin{cases} i_{cmd}^{(1)} = i_{cmd1}^{(1)} + i_{cmd2} \\ i_{cmd}^{(2)} = i_{cmd1}^{(2)} - i_{cmd2} \\ i_{cmd}^{(3)} = i_{cmd1}^{(3)} + i_{cmd2} \\ i_{cmd}^{(4)} = i_{cmd1}^{(4)} - i_{cmd2} \end{cases} \qquad \#(25)$$

$$\begin{cases} i_{cmd}^{(1)} = i_{cmd1}^{(1)} + i_{cmd2} \\ i_{cmd}^{(2)} = i_{cmd1}^{(2)} \\ i_{cmd}^{(3)} = i_{cmd1}^{(3)} + i_{cmd2} \\ i_{cmd}^{(4)} = i_{cmd1}^{(4)} \end{cases} \qquad \#(26)$$

Figure 8B:
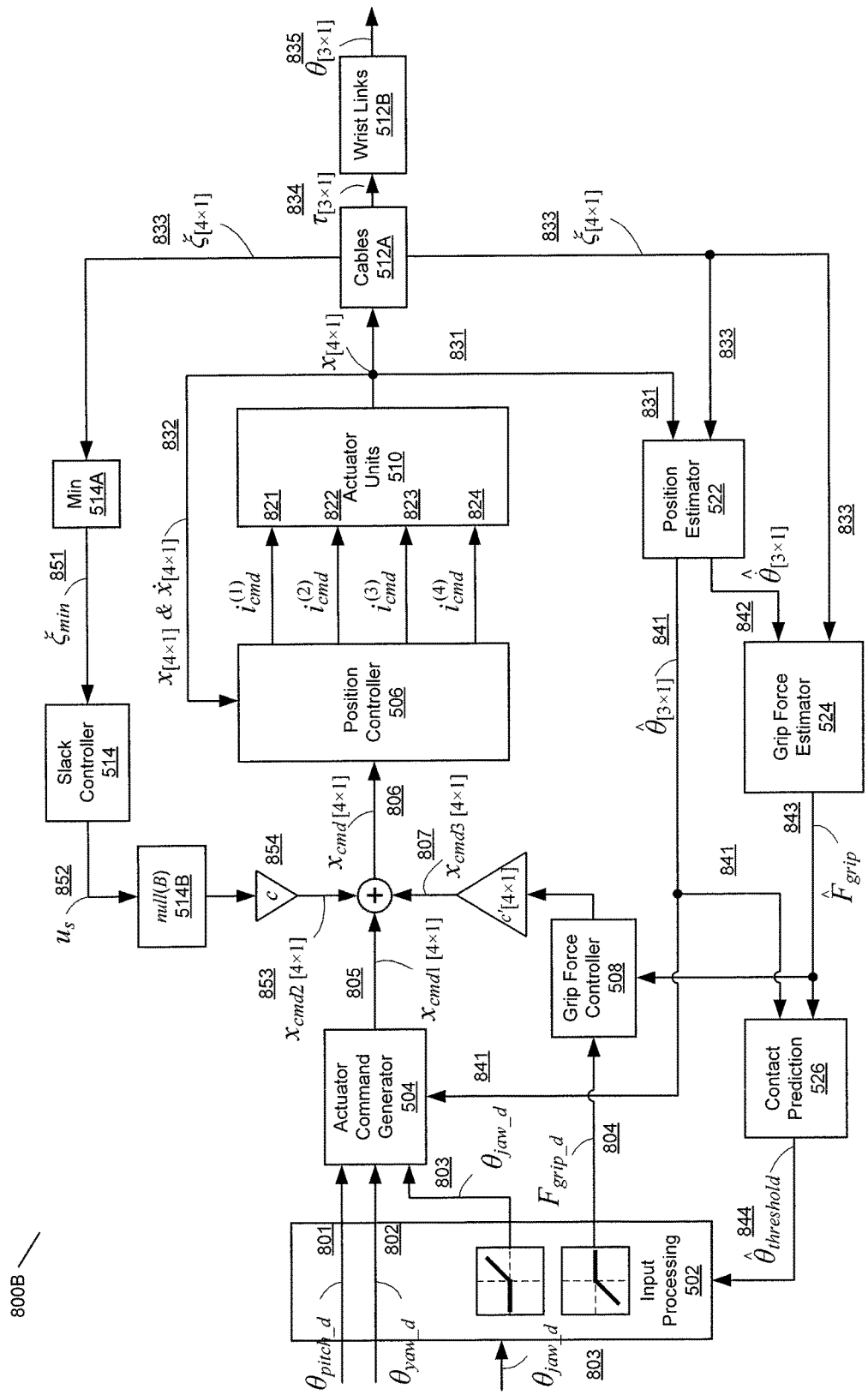

In some implementations, the grip force control algorithm may use a model to calculate the additional current needed for generating the desired grip force, rather than estimation based on the cable tension measurement. The model may project the grip force based on known parameters, such as motor position and current. FIG. 8B is a detailed block diagrams illustrating an alternative control system 800B for controlling the position and grip force of an end effector of a robotic surgical tool, in accordance with aspects of the subject technology. In the control system 800B, instead of generating additional current setpoints ($i_{cmd2}$) to be added to and subtracted from the current commands as shown in FIG. 8A, the grip force controller 508 may generate additional position setpoints, such as ($x_{cmd3}$) 807 shown in FIG. 8B, to be added to the two closing cables position setpoints and subtracted from the two opening cables position setpoints (or vice versa). Therefore the position input command ($x_{cmd}$) 806 to the position controller 506 may include three components: the first component ($x_{cmd1}$) 805 generated by the actuator command generator 504 outlined above, a second component ($x_{cmd2}$) provided by the slack controller 514, and third component ($x_{cmd3}$) 807 calculated by the grip force controller 508. The composite position command ($x_{cmd}$) 806 is provided to the position controller 506 for generating current command ($i_{cmd}$) for driving the actuator units 510.

Figure 9:
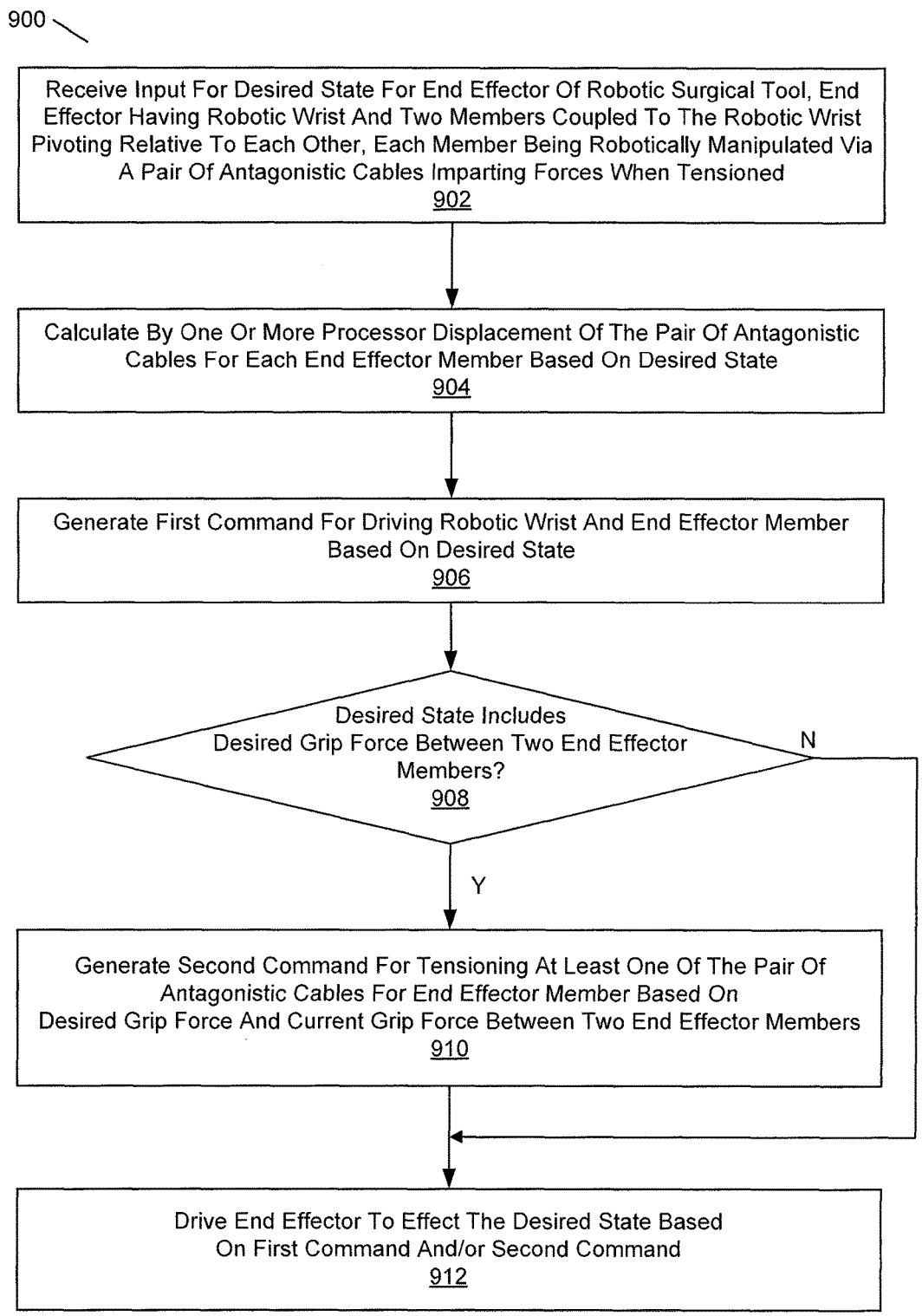
FIG. 9 is a flowchart illustrating an example process for controlling a robotic surgical tool having an end effector with two opposing members, in accordance with aspects of the subject technology.

FIG. 9 is a flowchart illustrating an example process 900 for controlling a robotic surgical tool having an end effector with two opposing members, in accordance with aspects of the subject technology. It should be understood, however, that the process 900 performed by the surgical tool control system provides only an illustrative description of the operation of the controller, and that more or fewer steps may be included in the process, and/or the steps may occur in one or more orders which are different from the order of blocks shown in FIG. 9.

First, the surgical tool control system receives 902 an input for a desired state for an end effector of a robotic surgical tool, the end effector having a robotic wrist at a distal end and two members coupled to the robotic wrist pivoting relative to each other. The desired state may comprise desired angles, such as a desired pitch angle of the robotic wrist, a desired yaw angle of the end effector, and a desired jaw angle between the two opposing members of the end effector. For example, in the tool control system 500 shown in FIG. 5, the input processing unit 502 may receive desired angular positions of the robotic wrist and end effector members. Each of the two opposing members may be robotically manipulated via a pair of antagonistic cables imparting forces when tensioned. For example, the end effector of the grasper 220 shown in FIG. 4A includes a pair of jaws 401A and 401B, and cables 405A and 405B are the first antagonistic pair for manipulating jaw 401A. When tensioned individually, cable 405A closes jaw 401A, while cable 405B opens jaw 401A.

The tool control system may subsequently calculate 904 a displacement of the pair of the antagonistic cables for each member of the end effector based on the desired state. In case the desired jaw angle indicates desired grip force, the displacement is calculated in response to the desired pitch and yaw angles. Otherwise, the displacement calculation corresponds to the desired pitch, yaw and jaw angles. In both cases, the position controller 506 in the tool control system, as shown in FIGS. 8A and 8B, may also base the calculation upon measurements of the current positions and/or velocity of the at least one actuator. Next, the control system may generate 906 a first command for driving the robotic wrist and the end effector members based on the calculated displacement. For example, the actuator command generator 504 in FIGS. 8A and 8B can generate displacement or positions command ($x_{cmd1}$) based on desired pitch and yaw angles (as well as jaw angle in case it represents desired angle instead of desired grip force). The control system may also optionally adopt another feedback control loop to prevent cable slack, such as the slack controller 514 in FIGS. 8A and 8B, to monitor the tensioning forces on the pair of antagonistic cables and to maintain a predetermined minimum tensioning force on the cables. The output ($x_{cmd2}$) from the slack controller 514 can be summed up with the position command ($x_{cmd1}$) to provide to the position controller 506 as the position setpoint.

The surgical tool control system may then determine 908 whether the desired state includes a desired grip force between the two opposing members of the end effector. In some implementations, to determine whether the desired state include a desired grip force may involve comparing the desired jaw angle to a threshold. The threshold can be a contact jaw angle between the two opposing members of the end effector when grasping an object or when in contact to each other without grasping any object (i.e., zero degree). For example, when the grasper 220 is not grasping any objects, the contact angle is zero degree. The contact angle can be predetermined, for instance, based on the size of the object to be grasped. Alternatively or in addition, the contact angle can be determined dynamically or predicted based on the estimation of current jaw angle and/or the estimation of a current grip force between the two opposing members, for example, by the contact prediction unit 526 shown in FIGS. 8A and 8B. When the desired jaw angle is smaller than the threshold, the desired jaw angle can be interpreted both as an indication and an extent of the desired grip force between the two opposing members of the end effector.

In response to a determination that the desired state includes a desired grip force (e.g., when the desired jaw angle is smaller than the threshold), the tool control system may generate 910 a second command for tensioning at least one of the pair of antagonistic cables for a member of the end effector based on the desired grip force indicated by the desired jaw angle and the current grip force between the two end effector members. As described above, each of the pair of antagonistic cables (e.g., cables 405A and 405B in FIG. 4A) for a member of the end effector (e.g., jaw 401A in FIG. 4A) can be pulled or tensioned by at least one actuator, such as the rotary drives 322A-322F shown in FIG. 3B. The second command can be calculated, for example, by the grip force controller 508 shown in FIGS. 8A and 8B, based on the difference between the desired grip force 804 and an estimation of the current grip force 843 from the grip force estimator 524, which may take into consideration the measurements of the current tensioning forces 833 on the pair of antagonistic cables, as well as angular velocity 842 from the position estimator 522.

In block 912, the tool control system drives the end effector to effect the desired state based on the first command and/or the second command. In some implementations as shown in FIG. 8A, the tool control system may generate a first current command ($i_{cmd1}$) for the at least one actuator based on the calculated displacement to drive the end effector. In case it is determined that the desired jaw angle indicates a desired grip force, a second drive command ($i_{cmd2}$) is generated for the at least one actuator based on the desired grip force and the estimated current grip force. The actual input to the actuator units 510, for example, may be a composite command based on the first drive command and the second drive command to drive the at least one actuator. The composite command can be any linear combination of the first and the second commands, as illustrated in Eqs. (23)-(26). In some other implementations as shown in FIG. 8B, the grip force controller 508 outputs an additional displacement or position command ($x_{cmd3}$), which is combined with the position setpoints from the actuator command generator 504 and slack controller 514 to generate a composite position command ($x_{cmd}$). The composite position command can then be input to the position controller 506 for generating current commands to drive the actuator units 510.

FIG. 10 is a flowchart illustrating another example process 1000 for controlling a robotic surgical tool having an end effector with two opposing members, in accordance with aspects of the subject technology. In this example, the surgical robotic system comprises a robotic surgical tool having an end effector at a distal end. The end effector has two opposing jaws each manipulated by at least one actuator via a pair of antagonistic cables imparting forces when tensioned by the actuator. The system may also include a controller comprising one or more processors coupled to the robotic surgical tool.

The controller may receive 1002, from an input module, an input to effect a desired state of the end effectors of the robotic surgical tool. The input may include at least one of a pitch angle and a yaw angle of the end effector, and a jaw angle between the two jaws of the end effector. The controller then determines 1004 a desired position of the end effector based on the pitch angle and the yaw angle, and a desired grip force between the two jaws of the end effector based on the jaw angle. Based on the desired position and desired grip force, the controller can drive 1006 the at least one actuator to effect the desired state of the tool, including the desired position of the end effector and the desired grip force between the jaws.

In some implementations, to effect the desired state of the tool, the controller may measure the current positions of the at least one actuator as well as current tensioning forces on the pair of antagonistic cables to generate a first drive command for the at least one actuator. The controller may further estimate a current grip force between the two opposing members of the end effector based on the measured tensioning forces on the pair of antagonistic cables to generating a second drive command for the at least one actuator. The first and the second drive commands may be combined to drive the tool to the desired state.

Figure 11:
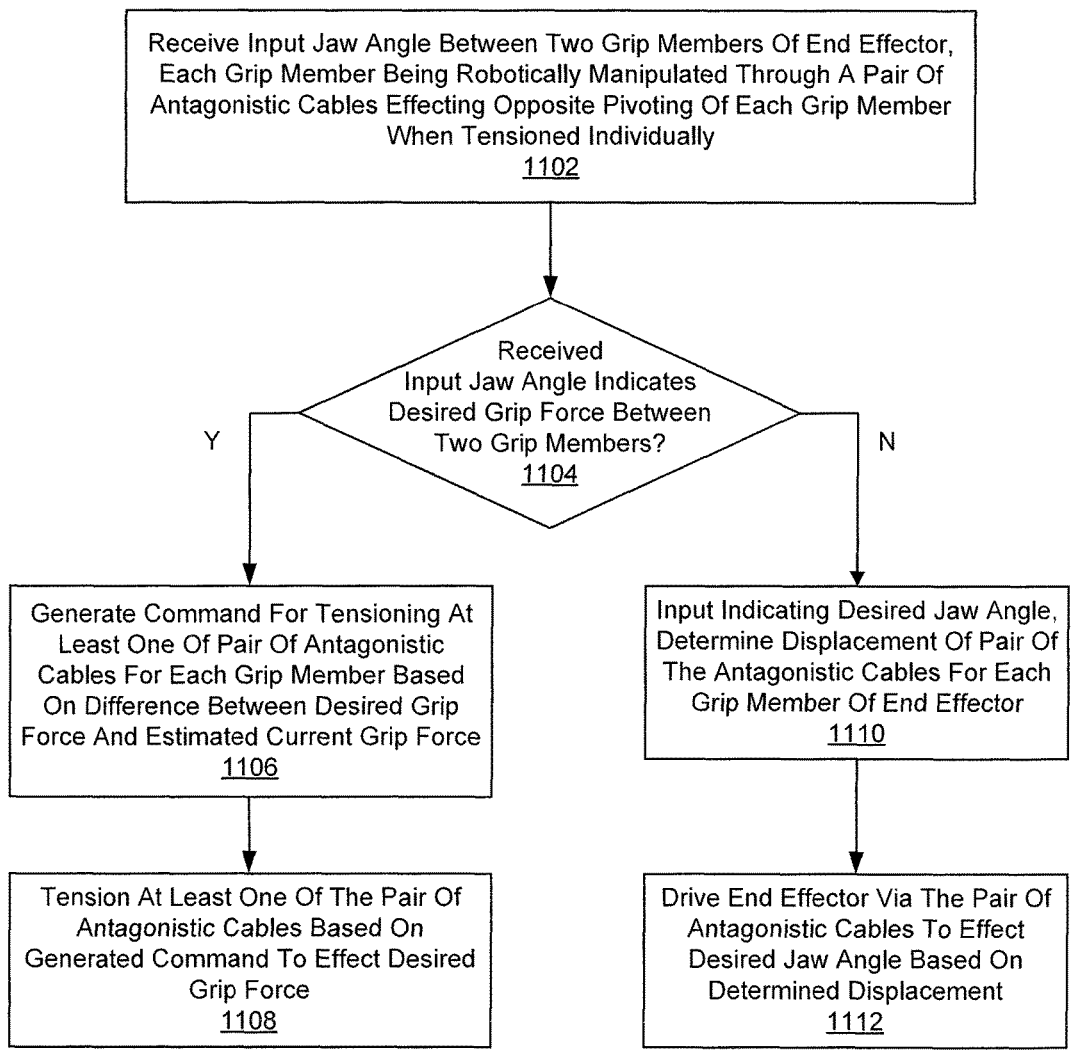
FIG. 11 is a flowchart illustrating yet another example process for controlling a robotic surgical tool having an end effector with two grip members, in accordance with aspects of the subject technology.

FIG. 11 is a flowchart illustrating yet another example process 1100 for controlling a robotic surgical tool having an end effector with two grip members, in accordance with aspects of the subject technology. As shown in FIG. 11, the example robotic surgical tool control system comprises a surgical tool having an end effector with two grip members, each of which is robotically manipulated through a pair of antagonistic cables effecting opposite pivoting of each grip member when tensioned individually. The tool control system also comprises one or more processors and an input coupled to the processors.

The tool control system may receive 1102 an input jaw angle between the two grip members of the end effector. Next, the tool control system may determine 1104 whether the received input jaw angle indicates a desired grip force between the two grip members. For example, the command indicates a desired grip force when the desired jaw angle is smaller than a threshold, which can be a contact angle between the two grip members when the end effector is grasping an object. In some implementations, the contact angle can be determined based on an estimation of a current grip forces between the two grip members and an estimation of a current jaw angle.

In response to a determination that the desired jaw angle indicates a desired force, the tool control system may generate 1106 a command for tensioning at least one of the pair of antagonistic cables for each grip member based on the difference between the desired grip force and an estimation of the current grip force. For example, the input jaw angle indicates a desired grip force when the input jaw angle is smaller than a threshold, which is a contact jaw angle between the two grip members when the end effector is grasping an object or zero degree when not grasping. The contact angle can be determined based on an estimation of the current grip force between the two grip members and an estimation of the current jaw angle. In some implementations, the current grip force between the two grip members can be estimated based on the measurements of the current tensioning forces on the pair of antagonistic cables. The at least one of the pair of antagonistic cables can then be tensioned 1108 to effect the desired grip force.

Otherwise if it is determined that the received input is indeed a desired jaw angle (e.g., the input jaw angle exceeds the threshold), the tool control system may determine 1110 a displacement of the pair of the antagonistic cables for each grip member of the end effector, and drive 1112 the end effector via the pair of antagonistic cables to effect the desired jaw angle based on the determined displacement.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry.

For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. A method for controlling a robotic surgical tool during robotic surgery, comprising:
receiving an input for a desired state for a distal end effector of a robotic surgical tool, the distal end effector having a robotic wrist and two distal end effector members coupled to the robotic wrist pivoting relative to each other, each distal end effector member being robotically manipulated via a pair of antagonistic cables imparting forces when tensioned;

calculating, by one or more processors, displacements of each pair of antagonistic cables based on the desired state;

generating a first command for position control to drive the robotic wrist and the distal end effector members based on the calculated displacements;

determining whether the desired state includes a desired grip force between the two distal end effector members;

responsive to a determination of the desired grip force, generating a second command for grip force control to tension at least one of the pair of antagonistic cables based on the desired grip force and a current grip force between the two distal end effector members, wherein the current grip force between the two distal end effector members is estimated based on measurements of current tensioning forces on the pairs of antagonistic cables using load cells or torque sensors;

generating a composite command by adding the second command for grip force control to the first command for position control; and driving the distal end effector to effect the desired state based on the composite command, wherein the composite command provides simultaneous grip force control and position control for various degrees of freedom of the distal end effector.

2. The method of claim 1, wherein the desired state comprises at least one of a desired pitch angle of the robotic wrist, a desired yaw angle of the distal end effector and a desired jaw angle between the two opposing members of the distal end effector.

3. The method of claim 2, wherein determining whether the desired state includes a desired grip force comprises comparing the desired jaw angle to a threshold.

4. The method of claim 3, wherein the threshold is a contact jaw angle between the two opposing members of the distal end effector when grasping an object or when in contact with each other without grasping any objects.

5. The method of claim 4, wherein the contact jaw angle is determined based on the estimation of the current grip force between the two opposing distal end effector members and an estimation of current jaw angle.

6. The method of claim 1, wherein each of the pair of antagonistic cables is tensioned by at least one actuator.

7. The method of claim 6, wherein calculating the displacement further comprises:

measuring current positions and/or velocity of the at least one actuator and current tensioning forces on each pair of antagonistic cables; and estimating a current state of at least one of a pitch angle of the robotic wrist, a yaw angle of the distal end effector, a jaw angle between the two opposing members of the distal end effector, and a current grip force based on the measurements.

8. The method of claim 6, wherein the composite command drives the at least one actuator.

9. The method of claim 1, further comprising:

monitoring tensioning forces on each pair of antagonistic cables; and maintaining a predetermined minimum tensioning force on each pair of antagonistic cables to prevent cable slack.

10. A surgical robotic system, comprising:

a robotic surgical tool having an end effector at a distal end, the end effector comprising two opposing jaws each manipulated by a pair of actuators and a pair of antagonistic cables imparting forces when tensioned by the pair of actuators; and a controller comprising one or more processors coupled to the robotic surgical tool, the processors configured to:

receive, from an input module, an input to effect a desired state of the end effector, the input including at least one of a pitch angle and a yaw angle of the end effector, and a jaw angle between the two jaws;

measure positions of the pair of actuators and tensioning forces on the pair of antagonistic cables;

determine a desired position of the end effector based on the pitch angle and the yaw angle, and a desired grip force between the two jaws based on the jaw angle;

generate a first drive command for each of the pair of actuators based on the desired position and the measured positions and tensioning forces;

estimate a current grip force between the two opposing jaws based on the measured tensioning forces on the pairs of antagonistic cables;

generate a second drive command for each of the pair of actuators based on a difference between the desired grip force and the estimated current grip force; and drive the pair of actuators to effect the desired position and the desired grip force using a composite drive command based on a summation of the first drive command and the second drive command.

11. A robotic surgical tool control system, comprising:

a distal end effector of a surgical tool having two grip members, each grip member being robotically manipulated through a pair of antagonistic cables effecting opposite pivoting of each grip member when tensioned individually;

an input for receiving an input jaw angle between the two grip members of the distal end effector; and one or more processors configured for:

generating a first command for position control to drive the surgical tool;

determining whether the received input jaw angle indicates a desired grip force between the two grip members;

responsive to a determination of the desired grip force, generating a second command for grip force control to tension at least one of the pair of antagonistic cables for each grip member based on a difference between the desired grip force and an estimated current grip force, wherein the current grip force is estimated based on measurements of current tensioning forces on the pairs of antagonistic cables using load cells or torque sensors;

generating a composite command by adding the second command for grip force control to the first command for position control; and tensioning the at least one of the pair of antagonistic cables based on the generated composite command to effect the desired grip force, wherein the generated composite command provides simultaneous grip force control and position control for various degrees of freedom of the distal end effector.

12. The system of claim 11, wherein the input indicates a desired grip force when the input jaw angle is smaller than a threshold, wherein the threshold is a contact jaw angle between the two grip members when the distal end effector is grasping an object or zero degrees when not grasping.

13. The system of claim 12, wherein the contact angle is determined based on the estimation of the current grip force between the two grip members and an estimation of a current jaw angle.

14. The system of claim 11, wherein the processors are further configured for:
- responsive to determining that the received input indicates a desired jaw angle, determining a displacement of the pair of the antagonistic cables for each grip member of the distal end effector; and
- driving the distal end effector via the pair of antagonistic cables to effect the desired jaw angle based on the determined displacement.

* * * * *

UNITED STATES PATENT AND TRADEMARK OFFICE
CERTIFICATE OF CORRECTION

PATENT NO.       : 10,166,082 B1
APPLICATION NO.  : 15/983946
DATED            : January 1, 2019
INVENTOR(S)      : Alireza Hariri et al.

Page 1 of 3

It is certified that error appears in the above-identified patent and that said Letters Patent is hereby corrected as shown below:

In the Specification

In Column 6, Line 56, delete "42C" and insert in its place --425C--.

In Column 8, Line 36, in equation (1), delete "#" before "(1)".

In Column 8, Line 46, in equation (2), delete "#" before "(2)".

In Column 9, Line 2, delete "#" and insert in its place --≠--.

In Column 9, Line 3, delete "wells" and insert in its place --well--.

In Column 9, Line 7, in equation (3), delete "#" before "(3)".

In Column 9, Line 12, in equation (4), delete "#" before "(4)".

In Column 9, Line 19, in equation (5), delete "#" before "(5)".

In Column 9, delete equation (5) and insert in its place --$\xi_{[4\times1]} = [\xi_1\ \xi_2\ \xi_3\ \xi_4]^T$--.

In Column 9, Line 25, in equation (6), delete "#" before "(6)".

In Column 9, delete equation (6) and insert in its place --$\tau_{[3\times1]} = [\tau_1\ \tau_2\ \tau_3]^T$--.

In Column 9, Line 32, in equation (7), delete "#" before "(7)".

In Column 9, delete equation (7) and insert in its place --$q_{[4\times1]} = [q_1\ q_2\ q_3\ q_4]^T = B^T \cdot \theta_{[3\times1]}$--.

In Column 9, Line 37, in equation (8), delete "#" before "(8)".
In Column 9, delete equation (8) and insert in its place --$\theta_{[3\times1]} = [\theta_1\ \theta_2\ \theta_3]^T$--.

Signed and Sealed this
Tenth Day of December, 2019

Andrei Iancu
*Director of the United States Patent and Trademark Office*

In Column 9, Line 41, in equation (9), delete "#" before "(9)".

In Column 9, delete equation (9) and insert in its place --$\xi_{[4\times1]} = k_e(x_{[4\times1]} - B^T \cdot \theta_{[3\times1]})$--.

In Column 11, Line 12, delete "," between "together" and "with".

In Column 11, Line 13, delete "jaw" and insert in its place --yaw--.

In Column 14, Line 38, in equation (10), delete "#" before "(10)".

In Column 14, Line 56, in equation (11), delete "#" before "(11)".

In Column 14, Line 62, in equation (12), delete "#" before "(12)".

In Column 14, delete equation (12) and insert in its place --$x_{[4\times1]} = [x_1 \; x_2 \; x_3 \; x_4]^T$--.

In Column 15, Line 7, in equation (13a), delete "##" before "(13a)".

In Column 15, delete equation (13a) and insert in its place --$x_{cmd1[4\times1]} = q_{d[4\times1]} = B^T \cdot \theta_{d[3\times1]}$--.

In Column 15, Line 13, in equation (13b), delete "##" before "(13b)".

In Column 15, Line 17, in equation (14), delete "#" before "(14)".

In Column 15, Line 29, in equation (15), delete "#" before "(15)".

In Column 15, delete equation (15) and insert in its place --$\xi_{min} = min(\xi_1, \xi_2, \xi_3, \xi_4)$--.

In Column 15, Line 40, in equation (16a), delete "#" before "(16a)".

In Column 15, Line 57, in equation (16b), delete "#" before "(16b)".

In Column 16, Line 1, in equation (17), delete "#" before "(17)".

In Column 16, Line 25, in equation (18), delete "#" before "(18)".

In Column 16, delete equation (18) and insert in its place

--$i_{cmd[4\times1]} = \begin{bmatrix} i_{cmd}^{(1)} & i_{cmd}^{(2)} & i_{cmd}^{(3)} & i_{cmd}^{(4)} \end{bmatrix}^T = i_{cmd1[4\times1]} + c_{i[4\times1]} \cdot i_{cmd2}$--.

In Column 16, Line 37, in equation (19a), delete "#" before "(19a)".

In Column 16, Line 56, in equation (19b), delete "#" before "(19b)".

In Column 16, delete equation (19b) and insert in its place $$i_{cmd1[4\times1]} = \begin{bmatrix} i^{(1)}_{cmd1} & i^{(2)}_{cmd1} & i^{(3)}_{cmd1} & i^{(4)}_{cmd1} \end{bmatrix}^T = -k_p(x_{[4\times1]} - x_{cmd[4\times1]}) - k_d \dot{x}_{[4\times1]}$$
--.

In Column 17, Line 9, in equation (20), delete "#" before "(20)".

In Column 17, Line 18, in equation (21), delete "#" before "(21)".

In Column 17, Line 40, in equation (22), delete "#" before "(22)".

In Column 17, delete equation (22) and insert in its place
-- $i_{cmd2} = k_{pg}(\hat{F}_{grip} - F_{grip_d}) + k_{ig} \int (\hat{F}_{grip} - F_{grip\_d})dt$ --.

In Column 17, Line 47 delete the equation before "821-824" and insert in its place
-- $(i^{(1)}_{cmd} \quad i^{(2)}_{cmd} \quad i^{(3)}_{cmd} \quad i^{(4)}_{cmd})$ --.

In Column 17, Line 60, in equation (23), delete "#" before "(23)".

In Column 18, Line 2, in equation (24), delete "#" before "(24)".

In Column 18, Line 8, in equation (25), delete "#" before "(25)".

In Column 18, Line 14, in equation (26), delete "#" before "(26)".

In Column 18, Line 25, after "current.", add a "¶".

In the Claims

In Column 23, Claim 6, Line 45, delete "of the".